United States Patent [19]

Comte et al.

[11] Patent Number: 5,021,420

[45] Date of Patent: Jun. 4, 1991

[54] DERIVATIVES OF (AZA)NAPHTHALENESULTAM, THEIR PREPARATION AND COMPOSITIONS CONTAINING THEM

[75] Inventors: Marie-Ihérèse Comte, Chevilly-Larue; Claude Gueremy, Houilles; Jean-Luc Malleron, Marcoussis; Serge Mignani, Livry-Gargan; Jean-Francois Peyronel, Palaiseau; Alain Truchon, Creteil, all of France

[73] Assignee: Rhone-Poulenc Sante, Antony, France

[21] Appl. No.: 375,934

[22] Filed: Jul. 6, 1989

[30] Foreign Application Priority Data

Jul. 7, 1988 [FR] France .................................. 88 09218
Feb. 20, 1989 [FR] France .................................. 89 02167

[51] Int. Cl.$^5$ ................. A61K 31/495; A61K 31/445; C07D 403/00; C07D 417/06
[52] U.S. Cl. ............................ 514/253; 514/228.2; 514/232.8; 514/321; 514/338; 544/61; 544/121; 544/124; 544/129; 544/130; 544/360; 544/368; 544/372; 546/187; 546/198; 546/199; 546/201; 546/271; 548/208
[58] Field of Search ................. 544/368, 61, 121, 124, 544/129, 130, 360, 372; 546/187, 198, 270, 199, 201, 271; 514/228.2, 232.8, 253, 321, 338; 548/208

[56] References Cited

U.S. PATENT DOCUMENTS 3,575,990   4/1971   Hermans et al. ................. 546/217
4,770,989   9/1988   Komamura et al. ............. 430/557

FOREIGN PATENT DOCUMENTS 0110435   6/1984   European Pat. Off. .
2139084   2/1973   Fed. Rep. of Germany .

OTHER PUBLICATIONS

A. Mustafa et al., Arch. Pharm., 298, 741, (1965).
F. Dannerth et al., J. Am. Chem. Soc., 29, 1319, (1907).

(List continued on next page.)

Primary Examiner—Cecilia Shen
Attorney, Agent, or Firm—Morgan & Finnegan

[57] ABSTRACT

This invention relates to a compound

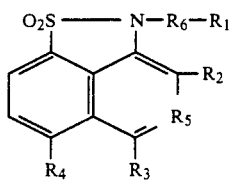

in which
$R_1$ represents
a 1,2,3,6-tetrahydro-1-pyridyl radical substituted in the 4-position by (a) a phenyl radical, (b) a phenyl radical substituted by a halogen atom or an alkyl, hydroxy or alkoxy radical, (c) a 3-indolyl radical, (d) a 3-indolyl radical substituted on the nitrogen atom by an alkyl or alkylcarbonyl radical and/or in the 5-position by a halogen atom or (e) a 3-(5-hydroxyindolyl) radical.
a 1-piperazinyl radical substituted in the 4-position by (a) a phenyl radical, (b) a phenyl radical substituted by an alkoxy, alkyl, hydroxy, nitro or amino radical or a halogen atom, (c) a 1,2-benzisothiazol-3-yl radical, (d) a 1,2-benzisoxazol-3-yl radical or (e) a 2-pyridyl radical.
a piperidino radical substituted in the 4-position by (a) a phenyl radical, (b) a phenyl radical substituted by a halogen atom or a hydroxy, alkyl or alkoxy radical, (c) two phenyl radicals, (d) a bis(4-fluorophenyl)methylene radical, (e) a 4-fluorobenzoyl radical, (f) a 2-oxo-1-benzimidazolinyl radical, (g) a 2-oxo-1-benzimidazolinyl radical substituted in the 3-position by an alkylcarbonyl or benzoyl radical, (h) a hydroxy radical and a phenyl radical optionally substituted with an alkyl, alkoxy or hydroxy radical or a halogen atom, (i) a 3-indolyl radical, (j) a 3-indolyl radical substituted on the nitrogen atom by an alkyl or alkylcarbonyl radical and/or in the 5-position by a halogen atom or (k) a 3-(5-hydroxyindolyl) radical.
either:
$R_2$ and $R_3$, which are identical, represent a hydrogen or halogen atom and $R_4$ represents a hydrogen atom or
$R_2$ and $R_4$ represent a hydrogen atom and $R_3$ represents a halogen atom or an acetylamino radical or
$R_2$ and $R_3$ represent a hydrogen atom and $R_4$ represents a halogen atom and $R_5$ represents a —CH= group.
or $R_2$, $R_3$ and $R_4$ represent a hydrogen atom and $R_5$ represents a nitrogen atom.
$R_6$ represents an alkylene chain containing 2 to 4 carbon atoms or a propylene chain substituted in the 1- or 3-position by an alkyl radical or in the 2-position by an alkyl, alkoxy, hydroxy, dialkylamino, piperidino, morpholino or thiomorpholino radical,
with the reservation that when $R_6$ represents a propylene radical substituted in the 2-position by a dialkylamino, piperidino, morpholino or thiomorpholino radical, $R_1$ cannot be a radical containing a hydroxy radical, and their salts, are useful in therapy for their ability to block serotonin receptors.

6 Claims, No Drawings

OTHER PUBLICATIONS

P. Friedlander et al., Chem. Ber., 55B, 45, (1922).
Th. Zincke et al., Liebigs Ann. Chem., 411, 195, (1916).
M. D. Nair et al., Indian J. Chem. Soc., 5, 224, (1967).
Y. Haramoto et al., J. Chem. Soc. Chem. Comm., 75, (1983).
D. E. Horning et al., Can. J. Chem., vol. 48, 975, (1970).
March, Advanced Organic Chemistry, p. 382, (1985), Wiley Interscience.
F. Sato et al., Chem. Lett., 99, (1980).
March, Advanced Organic Chemistry, 342, (1985), Wiley Interscience.
R. L. Duncan, et al., J. Med. Chem., 13, 1, (1970).
D. K. Yung et al., J. Med. Chem., 21, 1301, (1978).
L. Nedelec et al., Eur. J. Med. Chem., 22, 33, (1987).
J. P. Yevich et al., J. Med. Chem., 29, 3, 359, (1986).
L. Thunus et al., Ann. Pharm., 38, 353, (1980).
J. Gootjes et al., Azneim Forsch., 17, 1145, (1967).
J. Bergman et al., J. Het. Chem., 1071, (1970).
Ahmed Mustaga et al., Chem. Abst., 51-12046f, (1957).
D. R. Maulding et al., Chem. Abst., 68-38860x, (1968).

DERIVATIVES OF (AZA)NAPHTHALENESULTAM, THEIR PREPARATION AND COMPOSITIONS CONTAINING THEM

DESCRIPTION OF THE INVENTION

The present invention provides, as new compounds, the (aza)naphthalenesultam derivatives of formula:

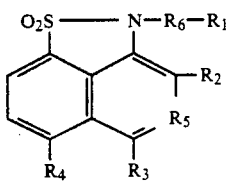
(I)

in which $R_1$ represents 1,2,3,6-tetrahydro-1-pyridyl radical substituted in the 4-position by (a) a phenyl radical, (b) a phenyl radical substituted by a halogen atom or an alkyl, hydroxy or alkoxy radical, (c) a 3-indolyl radical, (d) a 3-indolyl radical substituted on the nitrogen atom by an alkyl or alkylcarbonyl radical and/or in the 5-position by a chlorine or fluorine atom or (e) a 3-(5-hydroxyindolyl) radical, a (1)-piperazinyl radical substituted in the 4-position by (a) a phenyl radical, (b) a phenyl radical substituted by an alkoxy, alkyl, hydroxy, nitro or amino radical or a halogen atom, (c) a ,2-benzisothiazol-3-yl radical, (d) a ,1,2-benzisoxazol-3-yl radical or (e) a 2-pyridyl radical, a piperidino radical substituted in the 4-position by (a) a phenyl radical, (b) a phenyl radical substituted by a halogen atom or a hydroxy, alkyl or alkoxy radical, (c) two phenyl radicals, (d) a bis(4-fluorophenyl)methylene radical, (e) a 4-fluorobenzo-yl radical, (f) a 2-oxo-1-benzimidazolinyl radical, (g) a 2-oxo-1-benzimidazolinyl radical substituted in the 3-position by an alkylcarbonyl or benzoyl radical, (h) a hydroxy radical and a phenyl radical optionally substituted with an alkyl, alkoxy or hydroxy radical or a halogen atom, (i) a 3-indolyl radical, (j) a 3-indolyl radical substituted on the nitrogen atom by an alkyl or alkylcarbonyl radical and/or in the 5-position by a chlorine or fluorine atom or (k) a 3-(5-hydroxyindolyl) radical, either:
$R_2$ and $R_3$, which are identical, represent a hydrogen or halogen atom and $R_4$ represents a hydrogen atom or $R_2$ and $R_4$ represent a hydrogen atom and $R_3$ represents a halogen atom or an acetylamino radical or $R_2$ and $R_3$ represent a hydrogen atom and $R_4$ represents a halogen atom and $R_5$ represents a —CH= group, or $R_2$, $R_3$ and $R_4$ represent a hydrogen atom and $R_5$ represents a nitrogen atom, $R_6$ represents an alkylene chain containing 2 to 4 carbon atoms or a propylene chain substituted in the 1- or 3-position by an alkyl radical or in the 2-position by an alkyl, alkoxy, hydroxy, dialkylamino, piperidino, morpholino or thiomorpholino radical, with the reservation that when $R_6$ represents a propylene radical substituted in the 2-position with a dialkylamino, piperidino, morpholino or thiomorpholino radical, $R_1$ cannot be a radical containing a hydroxy radical.

In the preceding definitions, and those mentioned below, the alkyl and alkoxy radicals and the alkyl and alkoxy portions each contain I to 4 carbon atoms in a straight or branched chain and the halogen atoms are preferably chlorine or bromine atoms.

The invention also provides the salts of compounds of formula (I) with inorganic or organic acids The compounds of formula (I) in which $R_1$, $R_2$, $R_3$, $R_4$ and $R_5$ have the meanings mentioned above, with the reservation that $R_1$ cannot be a 4-aminophenyl-1-piperazinyl radical, and/or $R_6$ cannot be a propylene radical substituted in the 2-position by a dialkylamino, piperidino, morpholino or thiomorpholino radical, may be prepared by the action of a halogenated derivative of formula:

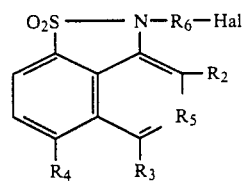
(II)

in which $R_2$, $R_3$, $R_4$, $R_5$ and $R_6$ have the same meanings as above and Hal represents a halogen atom on a compound of formula:

$$HR_1 \qquad (III)$$

in which $R_1$ has the same meanings as in formula (I) with the reservation that $R_1$ cannot be a 4-aminophenyl-1-piperazinyl radical or a salt of such a compound with an acid.

This reaction generally takes place in the presence of a base such as an alkali-metal carbonate or of an organic base such as 1,8-diazabicyclo[5,4,0]-7-undecene, 1,5-diazabicyclo[4,3,0]-5-nonene or triethylamine, optionally in the presence of sodium iodide, in an organic solvent such as benzene, toluene, dimethylformamide, acetonitrile, tetrahydrofuran or acetone, at a temperature of between 20° C. and the boiling point of the solvent.

The halogenated derivatives of formula (II) for which $R_5$ represents a —CH=, and either $R_2$, $R_3$ and $R_4$ represent a hydrogen atom, or $R_2$ and $R_3$ represent a halogen atom and $R_4$ represents a hydrogen atom, or $R_2$ and $R_4$ represent a hydrogen atom and $R_3$ represents a halogen atom, or $R_2$ and $R_3$ represent a hydrogen atom and $R_4$ represents a halogen atom, or even $R_5$ represents a nitrogen atom and $R_2$, $R_3$ and $R_4$ represent a hydrogen atom, and $R_6$ represents an alkylene (2-4 C.) radical or a propylene radical substituted in the 2-position by a hydroxy, alkyl or alkoxy radical can be prepared by the action of a compound of formula:

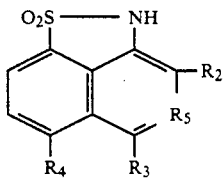

in which $R_2$, $R_3$, $R_4$ and $R_5$ have the same meanings as above, on a compound of formula:

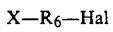

in which $R_6$ represents an alkylene (2-4 C.) radical or a propylene radical substituted in the 2-position by a hydroxy, alkyl or alkoxy radical, and Hal and X represent a halogen atom.

This reaction preferably takes place in the presence of a base such as an alkali-metal hydride, an alkali-metal hydroxide or an alkali-metal carbonate, in an inert solvent such as dimethylformamide or tetrahydrofuran, at a temperature of between 20° C. and the boiling point of the solvent.

The compounds of formula (IV) for which $R_5$ represents a =CH— group, $R_2$ and $R_4$ represent a hydrogen atom and $R_3$ represents a halogen atom, may be prepared by application or adaptation of the methods described by A. MUSTAFA et al., Arch. Pharm., 298, 741 (1965).

The compounds of formula (IV) for which $R_5$ represents a =CH—group, $R_2$ and $R_3$ represent a hydrogen atom and $R_4$ represents a halogen atom, may be prepared by cyclization of a compound of formula:

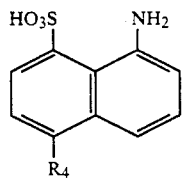

in which $R_4$ has the same meanings as above.

This cyclization is carried out, for example, by means of phosphorus oxychloride, at the boiling point of the reaction medium, by adaptation of the method described by F. DANNERTH et al., J. Am. Chem. Soc., 29, 1319 (1907).

The compounds of formula (VI) may obtained by application or adaptation of the method described by P. FRIEDLANDER et al., Chem. Ber., 55B, 45 (1922).

The compounds of formula (IV) for which $R_5$ represents a =CH— group, $R_2$ and $R_3$ represent a halogen atom and $R_4$ represents a hydrogen atom may be prepared by application or adaptation of the method described by Th. ZINCKE et al., Liebigs Ann. Chem., 411, 195 (1916).

The compound of formula (IV) for which $R_5$ represents a nitrogen atom may be obtained by cyclization of 4-bromo-5-isoquinolylsulphonamide.

This cyclization is preferably carried out by means of a base such as an alkali-metal hydride, in an inert organic solvent such as dimethylformamide or tetrahydrofuran, at a temperature of between 20° C. and the boiling point of the solvent.

4-Bromo-5-isoquinolylsulphonamide may be prepared by the action of ammonia on 4-bromo-5-isoquinolylsulphonyl chloride, preferably in tetrahydrofuran, at a temperature varying from −50° C. to 20° C.

4-Bromo-5-isoquinolylsulphonyl chloride may be prepared by the action of sodium nitrite on 5-amino-4-bromoisoquinoline in the presence of hydrochloric acid at a temperature of about 0° C., then of sulphur dioxide in acetic acid in the presence of cuprous chloride at a temperature of about 20° C.

5-Amino-4-bromoisoquinoline may be obtained by reduction of 4-bromo-5-nitroisoquinoline. This reduction is preferably carried out by means of stannous chloride and hydrochloric acid at the boiling point of the reaction mixture.

4-Bromo-5-nitroisoquinoline may be prepared by application of the method described by M.D. NAIR et al., Indian J. Chem. Soc., 5, 224 (1967).

The derivatives of formula (V) for which $R_6$ represents an alkylene (2-4 C.) radical or a propylene radical substituted in the 2-position by a hydroxy radical are commercially available.

The derivatives of formula (V) for which $R_6$ represents a propylene radical substituted in the 2-position by an alkyl radical may be obtained by application or adaptation of the method described by Y. HARAMOTO et al., J. Chem. Soc. Chem. Comm., 75 (1983).

The derivatives of formula (V) for which $R_6$ represents a propylene radical substituted in the 2-position by an alkoxy radical may be obtained by application or adaptation of the method described in Can. J. Chem., vol. 48, 975 (1970).

The halogenated derivatives of formula (II) for which $R_5$ represents a =CH— group, $R_2$ and $R_3$ represent a halogen atom and $R_4$ represents a hydrogen atom, and those for which $R_2$ and $R_4$ represent a hydrogen atom and $R_3$ represents a halogen atom and $R_6$ represents an alkylene (2-4 C.) radical, may also be obtained by halogenation of a compound of formula (II) in which $R_2$, $R_3$ and $R_4$ represent a hydrogen atom and $R_5$ represents a =CH— group, then optional separation of the monohalogenated derivative and the dihalogenated derivative.

The halogenation may be carried out by known methods such as those described by F. DERTH et al., J. Am. Chem Soc., 29, 1319 (1907), Th. ZINCKE et al., Ann. Chem., 411, 195 (1916) and A. MUSTAFA et al., Arch. Pharm., 298, 741 (1965).

The halogenated derivatives of formula (II) for which $R_2$, $R_3$, $R_4$ and $R_5$ have the same meanings as in formula (I), and $R_6$ represents a propylene radical substituted in the 1- or 3-position by an alkyl radical, with the exception of those for which $R_3$ represents an acetylamino radical, may be obtained by halogenation of a hydroxylated derivative of formula:

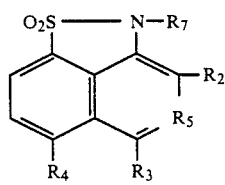

in which $R_2$, $R_3$, $R_4$ and $R_5$ have the same meanings as above and $R_7$ represents a 3-hydroxypropyl radical substituted in the 1-or 3-position by an alkyl radical.

This halogenation may be carried out according to processes known per se such as those described in MARCH, Advanced Organic Chemistry, p 382 (1985), Wiley Interscience.

This halogenation is preferably carried out by means of phosphorus tribromide or trichloride, in an inert solvent such as toluene, benzene or xylene, at a temperature of between 20° C. and the boiling point of the solvent.

The hydroxylated derivatives of formula (VII) may be prepared by the action of a derivative of formula (IV) in which $R_2$, $R_3$, $R_4$ and $R_5$ have the same meanings as in formula (VII), on a derivative of formula:

$$Br-R_7 \qquad \text{(VIII)}$$

in which $R_7$ has the same meanings as in formula (VII).

This reaction is generally carried out in the presence of a base such as an alkali-metal hydride, an alkali-metal hydroxide or an alkali-metal carbonate, in an inert solvent such as acetonitrile, dimethylformamide or tetrahydrofuran, at a temperature of 20° C. and the boiling point of the solvent.

The derivatives of formula (VIII) for which $R_7$ represents 3-hydroxypropyl radical substituted in the 1-position by an alkyl radical may be prepared by application or adaptation of the method described by D.A. PA-LAANDISHVLI et al., Chem. Abst., 70, 106089.

The derivatives of formula (VIII) for which $R_7$ represents a 3-hydroxypropyl radical substituted in the 1-position by an alkyl radical may be obtained by application or adaptation of the method described by F. SATO et al., Chem. lett., 99 (1980).

The halogenated derivatives of formula (II) for which $R_2$, $R_3$, $R_4$ and $R_5$ have the same meanings as in formula (I), with the reservation that $R_3$ cannot represent an acetylamino radical, and R represents a propylene radical substituted in the 2-position by an alkoxy radical may also be obtained by alkylation of the corresponding derivative of formula (II) for which $R_6$ represents a propylene radical substituted in the 2-position by a hydroxy radical.

This alkylation may be carried out according to the processes known per se such as those described in MARCH, Advanced Organic Chemistry, 342 (1985), Wiley Interscience.

For example an alkyl halide can be made to react in an inert solvent such as dimethylformamide or tetrahydrofuran, in the presence of an alkali-metal hydride or an alkali-metal carbonate, at a temperature of between 20° C. and the boiling point of the solvent.

The halogenated derivatives of formula (II) for which $R_5$ represents a =CH— group, $R_2$ and $R_4$ represent a hydrogen atom, $R_3$ represents an acetylamino radical and $R_6$ has the same meanings as above, may be prepared by N-acetylation of the corresponding amines.

The acetylation may be carried out by means of acetic anhydride, in the presence of an alkali-metal acetate, at the boiling point of the reaction medium.

The corresponding amines may be obtained by reduction of a derivative of formula:

(IX)

in which $R_6$ and Hal have the same meanings as in formula (II).

This reduction is carried out, for example, by means of nickel chloride and sodium borohydride, in an alcohol such as methanol or ethanol, at a temperature of about 0° C.

The nitrated derivatives of formula (IX) may be obtained by nitration of a compound of formula (II) in which $R_2$, $R_3$ and $R_4$ represent a hydrogen atom and $R_5$ represents a =CH— group.

This nitration is generally carried out, preferably by means of nitric acid, at a temperature of about 0° C.

Compounds of formula (III) are available commercially or may be prepared by application or adaptation of the methods described by R.L. DUNCAN et al., J. Med. Chem., 13, 1 (1970); D.K. YUNK et al., J. Med. Chem., 21, 1301 (1978); L. NEDELEC et al., Eur. J. Med. Chem., 22, 33 (1987); J.P. YEVICH et al., J. Med. Chem., 29, 3, 359 (1986); L. THUNUS et al., Ann. Pharm., 38, 353 (1980); L. GOOTES et al., Arzneim. Forsch., 17, 1145 (1967) and J. BERGMAN et al., J. Het. Chem. 1071 (1970) and in Patents DE 2139084, EP 110435 and U.S. Pat. No. 4,470,989 and 3,575,990 and of the methods described in the examples.

The 1-hydroxyphenylpiperazines may be obtained by demethylation of the corresponding 1-methoxyphenylpiperazines by any method known to those versed in the art, and in particular by means of hydrobromic acid.

The compounds of formula (I) in which
either $R_5$ represents a =CH— group, and $R_2$, $R_3$ and $R_4$ represent a hydrogen atom, or $R_2$ and $R_4$ represent a hydrogen atom and $R_3$ represents a halogen atom, or $R_2$ and $R_3$ represent a hydrogen atom and $R_4$ represents a halogen atom, or $R_2$ and $R_3$ represents a halogen atom and $R_4$ represents a hydrogen atom, or $R_5$ represents a nitrogen atom and $R_2$, $R_3$ and $R_4$ represent a hydrogen atom, $R_6$ represents an alkylene (2–4 C.) radical or a propylene radical substituted in the 2-position by a hydroxy, alkyl or alkoxy radical, except those for which $R_1$ is a 4-aminophenyl-1-piperazinyl radical, may also be prepared by the action of a compound of formula (IV) in which $R_2$, $R_3$, $R_4$ and $R_5$ have the meanings mentioned above, on a derivative of formula:

$$Hal-R_6-R_1 \qquad \text{(X)}$$

in which $R_6$ and $R_1$ have the same meanings as above and Hal represents a halogen atom.

This reaction is generally carried out in the presence of a base such as an alkali-metal hydride, an alkali-metal hydroxide or an alkali-metal carbonate, in an organic solvent such as dimethylformamide or tetrahydrofuran, or in the presence of an alkali-metal hydroxide in an aqueous or hydro-organic medium, at a temperature of between 20° C. and the boiling point of the solvent.

The derivatives of formula (X) may be prepared by the action of an alkyl dihalide of formula (V) on a compound of formula (III).

This reaction is generally carried out in the presence of an alkali-metal carbonate or a tertiary amine, in an organic solvent such as acetonitrile, at a temperature of about 20° C.

The compounds of formula (I) for which $R_6$ represents a propylene radical substituted in the 2-position by an alkoxy radical, with the exception of those for which $R_1$ represents a 1,2,3,6-tetrahydro-1-pyridyl radical substituted in the 4-position by a 3-indolyl radical, a 3-indolyl radical substituted in the 5-position by a hydroxy or hydroxyphenyl radical, a 1-piperazinyl radical substituted in the 4-position by an amino or hydroxyphenyl radical or a piperidino radical substituted in the 4-position by a 2-oxo-1-benzimidazolinyl, hydroxyphenyl, or hydroxy and phenyl radical optionally substituted by a hydroxy or 3-indolyl radical optionally substituted in the 5-position by a hydroxy radical may also be obtained by alkylation of the corresponding compounds of formula (I) for which $R_6$ represents a propylene radical substituted in the 2-position by a hydroxy radical.

This alkylation may be carried out under the same conditions as those described above for the alkylation of the halogenated derivatives of formula (II) for which $R_6$ represents a propylene radical substituted in the 2-position by a hydroxy radical.

The compounds of formula (I) for which $R_6$ represents a propylene radical substituted in the 2-position by a dialkylamino, piperidino, morpholino or thiomorpholino radical may be obtained by the action of a brominated derivative of formula:

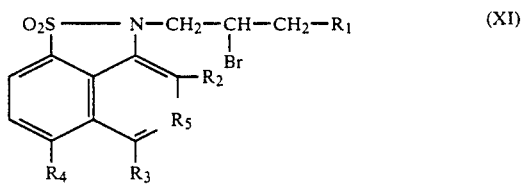

in which $R_2$, $R_3$, $R_4$, $R_5$ and $R_1$ have the same meanings as in formula (I) on a derivative of formula:

in which $R_8$ represents a dialkylamino, piperidino, morpholino or thiomorpholino radical.

This reaction is generally carried out in an inert solvent such as benzene, toluene or xylene, in the presence of a tertiary amine such as triethylamine, in a bomb at a temperature varying from 20° C. to the boiling point of the solvent The brominated derivatives of formula (XI) may be obtained by bromination of a corresponding derivative of formula (I) for which $R_7$ represents a propylene radical substituted in the 2-position by a hydroxy radical.

This bromination is carried out under the same conditions as those described above for the bromination of compounds of formula (VII).

The compounds of formula (I) for which $R_6$ represents a propylene radical substituted in the 3-position by a methyl radical, with the exception of those for which $R_3$ represents an acetylamino radical and/or $R_1$ represents a substituent containing a hydroxy radical, may also be obtained by the action of a derivative of formula (IV) on a derivative of formula:

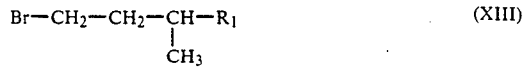

in which $R_1$ has the same meanings as above.

This reaction is generally carried out under the same Conditions as those mentioned above for the reaction of compounds of formula (IV) and (VII).

The derivatives of formula (XIII) may be obtained by bromination of a derivative of formula:

in which $R_1$ has the same meanings as above.

This bromination is preferably carried out under the same conditions as those described above for the bromination of compounds of formula (VII).

The derivatives of formula (XIV) may be obtained by the action of 3-bromo-1-butanol on a derivative of formula (III).

This reaction is generally carried out under the conditions described above for the reaction of derivatives of formulae (II) and (III).

The compounds of formula (I) for which $R_1$ represents a 1,2,3,6-tetrahydro-1-pyridyl radical substituted in the 4-position by a 3-indolyl radical substituted on the nitrogen atom by an alkyl or alkylcarbonyl radical, or a piperidino radical substituted in the 4-position by a 2-oxo-1-benzimidazolinyl radical substituted in the 3-position by an alkylcarbonyl or benzoyl radical, or a 3-indolyl radical substituted on a nitrogen atom by an alkyl or alkylcarbonyl radical, with the exception of those for which $R_6$ represents a propylene radical substituted in the 2-position by a hydroxy radical, may be obtained by the action of a derivative of formula:

in which Hal represents a halogen atom and $R_9$ represents an alkyl, alkylcarbonyl or benzoyl radical, on the corresponding derivatives of formula (I) for which $R_1$ represents a 1,2,3,6-tetrahydro-1-pyridyl radical substituted in the 4-position by a 3-indolyl radical, or a piperidino radical substituted in the 4-position by a 2-oxo-1-benzimidazolinyl or 3-indolyl radical.

This reaction is preferably carried out in an inert solvent such as dimethylformamide or tetrahydrofuran, at a temperature of between 20° C. and the boiling point of the solvent.

The compounds of formula (I) in which $R_1$ represents a 1,2,3,6-tetrahydro-1-pyridyl radical substituted in the 4-position by a phenyl radical substituted by a halogen atom may also be obtained by dehydration of a corresponding compound of formula (I) for which $R_1$ represents a 1,2,3,6-tetrahydro-1-pyridyl radical substituted in the 4-position by a hydroxy radical and a phenyl radical substituted by a halogen atom.

This dehydration may be carried out by known methods such as those described in MARCH, Advanced Organic Chemistry, 901 (1985), and particularly by means of sulphuric acid or of an acetic acid-hydrobromic acid, acetic acid-hydrochloric acid mixture at a temperature of between 20° C. and the boiling point of the reaction medium.

The compounds of formula (I) for which $R_1$ represents a 4-aminophenyl-1-piperazinyl radical may be obtained by reduction of the corresponding compounds of formula (I) for which $R_1$ represents a 4-nitrophenyl-1-piperazinyl radical.

This reduction is generally carried out by means of stannous chloride and sodium borohydride in an alcohol such as methanol or ethanol, in the presence of water, at a temperature of between 20° C. and 70° C. by mean of iron and hydrochloric acid in water or a water-alcohol mixture, at a temperature of between 20° C. and the boiling point of the reaction medium.

Compounds of formula (I) may be purified by the standard known methods such as crystallization or chromatography.

Compounds of formula (I), in the form of the free base, may be converted to addition salts with acids by the action of an acid in an organic solvent such as an alcohol, a ketone, a chlorinated solvent or an ether.

The compounds of formula (I) and their salts have useful properties. These compounds have antagonist properties towards serotonin ($5HT_2$ receptors) and are therefore useful for the treatment of ailments in which serotonin is implicated, and in particular ailments of the central nervous system and the cardiovascular system and gastrointestinal disorders.

These compounds are useful in particular for the treatment of anxiety, sleeping problems, depression, psychoses and in particular schizophrenia, migraine, asthma, hypertension and urticaria, as analgesics and as inhibitors of platelet aggregation.

The affinity of the compounds of formula (I) for the central serotinin receptor sites (type $S_2$) has been determined according to a technique inspired by that of J.E. LEYSEN et al., vol. Pharmacol., 21, 301 (1982), which consists in measuring the affinity of the products for the binding sites of tritiated ketanserin. In this test, the $IC_5O$ of compounds of formula (I) is generally less than 25 nM.

Compounds of formula (I) have low toxicity. They are generally atoxic at 300 mg/kg orally in the mouse in a single administration.

The compounds of formula (I) in which $R_1$ represents a 2,3,6-tetrahydro-1-pyridyl radical substituted in the 4-position by a halophenyl radical, a phenylradical or a 3-indolyl radical substituted on the nitro atom by alkyl or alkylcarbonyl radical a 1-piperazinyl radical substituted in the 4-position by a 2-pyridyl radical, 1,2-benzisothiazol-3-yl radical or phenyl radical substituted by a halogen atom or a hydroxy, amino or alkyl radical or a piperidino radical substituted in the 4-position by a phenyl or N-alkyl-3-indolyl radical are particularly interesting.

The following products are of particular interest :
-2-{3-[4-(1,2-benzisoxazol-3-yl)-1-piperazinyl]propyl}naptho[1,8-cd]isothiazole 1,1-dioxide
-2{-3-[4-(4-aminophenyl)-1-piperazinyl]propyl}naphtho [1,8-cd]isothiazole 1,1-dioxide
-2-{(3-[4-(3-fluorophenyl)-1-piperazinyl]propyl}naphthol[1,8-cd]isothiazole 1,1-dioxide
-2-{3-[4-4-methylphenyl)-1-piperazinyl]propyl}naphtho[1,8-cd]isothiazole 1,1-dioxide
-2-{3-[4-(3-hydroxyphenyl)-1-piperazinyl]propyl}naphtho[1,8-cd]isothiazole 1,1dioxide
-2-{3-[4-(1-methyl-3-indolyl)-1,2,3,6-tetrahydro-1-pyridyl]propyl}naphtho [1,8-cd]isothiazole 1,1-dioxide
-2-{3-[4-(1-acetyl-3-indolyl)-1,2,3,6-tetrahydro-1-pyridyl)propyl]naphtho}[1,8-cd]isothiazole 1,1, dioxide
-2-{2-[4-(4-hydroxyphenyl)-1-piperazinyl]ethyl}naphtho[1,8-cd]isothiazole 1,1-dioxide
-2-[3-{4-(4-fluorophenyl)-1-piperazinyl]propyl}naphtho[1,8-cd]isothiazole 1,1-dioxide
-2-{3-(4-phenyl-1,2,3,6-tetrahydro-1-pyridyl)propyl]-naphtho[1,8-cd]isothiazole 1,1-dioxide
-2-{3-[4-(4-fluorophenyl)-1,2,3,6-tetrahydro-1-pyridyl]-propyl}naptho [1,8-cd]isothiazole 1,1-dioxide
-2-{3-[4-(2-pyridyl)-1-piperazinyl]propyl}naphtho[1,8-cd]isothiazole 1,1-dioxide
-2-{3-(4-phenyl-1-piperidino)propyl]naphtho[1,8-cd]-isothiazole 1,1-dioxide
-2-{3-[4-(4-hydroxyphenyl)-1-piperazinyl]propyl)naphtho[1,8-cd]isothiazole 1,1-dioxide
-2-{3-[4-(4-fluorophenyl)-1-piperazinyl-2-hydroxypropyl)naphtho[1,8 cd]isothiazole 1,1-dioxide
-2-{3-[4-(4-fluorophenyl)-1-piperazinyl]-2-methoxypropyl}naphtho 1,8cd]isothiazole 1,1-dioxide
-2-{2-dimethyulamino-3-[4-(4-fluorophenyl)-1-piperazinyl]propyl}naphtho 1,8-cd]isothiazole 1,1-dioxide -2-{3-[4-(4-fluorophenyl)-1-piperazinyl]-2-methyl-propyl}naphtho[1,8-cd]isothiazole 1,1-dioxide
-2-{3-[4-(4-fluorophenyl)-1-piperazinyl]butyl)naphtho[1,8-cd]isothiazole 1,1-dioxide
-2-{4-[4-(4-fluorophenyl)-1-piperazinyl]-2-butyl)-naphtho[1,8-cd]isothiazole 1,1-dioxide For therapeutic use, compounds of formula (I) can be used as such or in the state of pharmaceutically acceptable salts.

Addition salts with inorganic acids, such as hydrochlorides, sulphates, nitrates or phosphates, or organic acids such as acetates, propionates, succinates, benzoates, fumarates, maleates, methanesulphonates, isothionates, theophyllineacetates, salicylates, phenolphthalinates or methylene-bis-$\beta$-oxynaphthoates, or substitution deriviates of these derivatives, may be mentioned in particular as pharmaceutically acceptable salts.

EXAMPLES

The following examples illustrate the invention.

EXAMPLE 1

2-(3-Chloropropyl)naphtho[1,8-cd]isothiazole 1,1-dioxide (28.1 g), triethylamine (14 cc) and 1-(4-fluorophenyl)piperazine (18.8 g) in toluene (300 cc) are heated for 8 hours at boiling point. The mixture is then cooled to a temperature of about 20° C. and stirring is maintained for 15 hours at this temperature. The precipitate formed is separated by filtration and washed with toluene (2 x 50 cc). The filtrate is evaporated to dryness at 40° C. under reduced pressure (20 mm Hg; 2.7 kPa). The residue obtained is purified by flash-chromatography on a silica column, under a current of argon at medium pressure (0.1–1.5 bar) with ethyl acetate as eluant, and recrystallized from boiling acetonitrile (150 cc). 2-{3-[4-(4-Fluorophenyl)-1piperazinyl]propyl} naphtho[1,8-cd]isothiazole 1,1-dioxide (37.8 g) is obtained, m.p. 95°–97° C.

2-(3-Chloropropyl)naphtho[1,8-cd]isothiazole 1,1-dioxide may be prepared in the following manner: a solution of 1,8-naphthosultam (175 g) in dimethylformamide (2100 cc) is poured, over 3 hours and 30 minutes, into a 50% dispersion of sodium hydride (40.2 g) in vaseline oil, under a current of argon, maintaining the temperature between 20° C. and 30° C. The reaction medium is stirred for 1 hour at a temperature of about 20° C., and then 1-bromo-3-chloropropane (83 cc) is added over 10 minutes. Stirring is maintained for 15 hours at a temperature of about 20° C. The reaction mixture is concentrated to dryness at 50° C. under reduced pressure (0.5 mm Hg; 0.7 kpa). The residue is purified by chromatography on a silica column with a mixture of dichloromethane and cyclohexane (60–40 vol) as eluant. 2-(3-Chloropropyl)naphtho[1,8-cd]isothiazole 1,1-dioxide (165.7 g) is obtained, m.p. 78° C.

EXAMPLE 2

The experiment is carried out as in Example 1, starting with 2-(3-chloropropyl)naphtho[1,8-cd]isothiazole 1,1-dioxide (2.8 g), triethylamide (1.4 cc) and 4-phenyl-1,2,3,6-tetrahydropyridine (1.6 g) in toluene (30 cc). The mixture is heated for 8 hours at boiling point, then cooled to a temperature of about 20° C. Stirring is continued for 15 hours at this temperature. After purification by flash-chromatography on a silica column, under a current of argon at medium pressure (0.5–1.5 bar) with ethyl acetate as eluant, and recrystallization from boiling isopropanol (20 cc), 2-[3-(4-phenyl-1,2,3,6-tetrahydro-1-pyridyl)propyl]naphtho[, 1,8-cd]isothiazole 1,1-dioxide (1.5 g) is obtained, m.p. 88° C.

EXAMPLE 3

The experiment is carried out as in Example 1, starting with 2-(3-chloropropyl)naphtho[1,8-cd]isothiazole 1,1-dioxide (100 g), triethylamine (50 cc) and 4-(4-fluorophenyl)-1,2,3,6-tetrahydropyridine (77.9 g) in toluene (950 cc). The mixture is heated for 7 hours at boiling point, then cooled to a temperature of about 20° C. Stirring is continued for 8 hours at this temperature. After purification by flash-chromatography on a silica column, under a current of argon at medium pressure (0.5–1.5 bar) with ethyl acetate as eluant, 2-{3-[4-(4-fluorophenyl)-1,2,3,6-tetrahydro -1-pyridyl]propyl}-naphtho [18-cd]isothiazole 1,1-dioxide (105.4 g) is obtained in the form of a brown oil [Rf=0.8; thin-layer chromatography on silica gel; eluant: ethyl acetate]. This oil is converted to the hydrochloride, m.p. 224° C.

EXAMPLE 4

The experiment is carried out as in Example 1, starting with 2-(3-chloropropyl)naphtho[1,8-cd]isothiazole 1,1-dioxide (8.5 g), triethylamine (4.2 cc) and 4-(4-chlorophenyl)-1,2,3,6-tetrahydropyridine (5.7 g) in toluene (80 cc). The mixture is heated for 8 hours at boiling point, then cooled to a temperature of about 20° C. Stirring is continued for 8 hours at this temperature. After purification by flash-chromatography on a silica column, under a current of argon at medium pressure (0.5–1.5 bar) with ethyl acetate as eluant, and recrystallization from boiling acetonitrile (50 cc), 2-3-[4-(4-chlorophenyl)-1,2,3,6-tetrahydro-1pyridyl]-propyl}naphtho[1,8-cd]isothiazole 1,1-dioxide (4.9 g) is obtained, m.p. 111° C.

EXAMPLE 5

The experiment is carried out as in Example 1, starting with 2-(3-chloropropyl)naphtho[1,8-cd]isothiazole 1,1-dioxide (8.5 g), triethylamine (4.2 cc) and 1-2-pyridyl)piperazine (4.7 cc) in toluene (80 cc). The mixture is heated for 2 hours at boiling point, then cooled to a temperature of about 20° C. After purification by flash-chromatography on a silica column, under a current of argon at medium pressure (0.5–1.5 bar) with ethyl acetate as eluant, and recrystallization from boiling acetonitrile (30 cc), 2-{3-[4-(2-pyridyl)-1-piperazinyl]propyl}naphtho[1,8-cd]isothiazole 1,1-dioxide (4.2 g) is obtained, m.p. 101° C.

EXAMPLE 6

The experiment is carried out as in Example 1, starting with 2-(3-chloropropyl)naphtho[1,8-cd]isothiazole 1,1-dioxide (8.5 g), triethylamine (4.2 cc) and N-phenyl-piperazine (4.8 cc) in toluene (80 cc). The mixture is heated for 8 hours at boiling point, then cooled to a temperature of about 20° C. After purification by flash-chromatography on a silica column, under a current of argon at medium pressure (0.5–1.5 bar) with ethyl acetate as eluant, and recrystallization from boiling acetonitrile (30 cc), 2-[3-(4-phenyl-1-piperazinyl)propyl]naphtho[1,8-cd]isothiazole 1,1-dioxide (5.7 g) is obtained, m.p. 126° C.

EXAMPLE 7

The experiment is carried out as in Example 1, starting with 2-(3-chloropropyl)naphtho[1,8-cd]isothiazole 1,1-dioxide (8.5 g), triethylamine (4.2 cc) and 4-phenyl-piperidine (4.9 g) in toluene (80 cc). The mixture is heated for 8 hours at boiling point, then cooled to a temperature of about 20° C. Stirring is continued for 15 hours at this temperature. After purification by flash-chromatography on a silica column, under a current of argon at medium pressure (0.5–1.5 bar) with ethyl acetate as eluant, and recrystallization from boiling acetonitrile (30 cc), 2-[3-(4-phenyl-1-piperidino)propyl]naphtho[1,8-cd]isothiazole 1,1-dioxide (7.1 g) is obtained, m.p. 125° C.

EXAMPLE 8

The experiment is carried out as in Example 1, starting with 2-(3-chloropropyl)naphtho[1,8-cd]isothiazole 1,1-dioxide (70.3 g), triethylamine (105 cc) and 1(4-hydroxyphenyl)piperazine dihydrobromide (85.2 g) in dimethylformamide (2100 cc). The mixture is heated for 8 hours at boiling point, then cooled to a temperature of about 20° C. Stirring.is continued for 6 hours at this temperature. After purification by flash-chromatography on a silica column, under a current of argon at medium pressure (0.5–1.5 bar) with dichloromethane and then a mixture of dichloromethane and ethyl acetate (50–50 vol) as eluant, and recrystallization from boiling acetonitrile (1150 cc), 2-{3-[4-(4-hydroxyphenyl)-1- piperazinyl]propyl}naptho[1,8-cd]isothiazole 1,1-dioxide (20.5 g) is obtained, m.p. 185° C.

1-(4-Hydroxyphenyl)piperezine dihydrobromide may be prepared in the following manner: a 47% aqueous solution of hydrobromic acid (720 cc) is added, over 30 minutes and at a temperature of about 20° C., to 4-(4-methoxyphenyl)piperazine dihydrochloride (70 g). The mixture is heated at boiling point for 4 hours then cooled to a temperature of about 20° C. Stirring is continued for 15 hours at this temperature, then the mixture is concentrated at 40° C. under reduced pressure (20 mm Hg; 2.7 kPa). The residual oil is redissolved in acetonitrile (300 cc). The precipitate formed is separated by filtration, washed with acetonitrile (2 x 50 cc) and diisopropyl ether (2 x 100 cc). 4-(4-Hydroxyphenyl)piperazine dihydrobromide (85.2 g) (m.p. greater than 260° C.) is obtained and used in the crude state in the subsequent syntheses.

EXAMPLE 9

The experiment is carried out as in Example 1, starting with 2-(3-chloropropyl)naphtho[1,8-cd]isothiazole 1,1-dioxide (4.2 g), triethylamine (2.1 cc), sodium iodide (2.2 g) and 4-(4-fluorobenzoyl)piperidine (3.1 g) in dimethylformamide (50 cc). The mixture is heated for 8 hours at boiling point, then cooled to a temperature of about 20° C. Stirring is continued for 7 hours at this temperature. After purification by flash-chromatography on a silica column, under a current of argon at medium pressure (0.5–1.5 bar) with ethyl acetate as eluant, and recrystallizatior from boiling acetonitrile (15 cc), 2-{3-[4-(4-fluorobenzoyl)piperidino]propyl}naphtho[1,8cd]isothiazole 1,1-dioxide (1.65 g) is obtained, m.p. 132° C.

4-(4-Fluorobenzoyl)piperidine may be prepared according to the method described by R.L. DUNCAN et al., J. Med. Chem., 13, 1 (1970).

EXAMPLE 10

The experiment is carried out as in Example 1, starting with 2-(3-chloropropyl)naphtho[1,8-cd]isothiazole 1,1-dioxide (5.3 g), triethylamine (2.6 cc), 4-(4-chlorophenyl)piperazine (5 g) and sodium iodide (2.8 g) in toluene (50 cc). The mixture is heated for 6 hours at boiling point, then cooled to a temperature of about 20° C. After recrystallization, firstly from boiling acetonitrile 6 hours and secondly from boiling methyl ethyl ketone (15 cc), 2-{3-[4-(4-chlorophenyl)-1-piperazinyl [propyl}naphtho[18-cd[isothiazole 1,1-dioxide (3 g) is obtained, m.p. 120° C.

EXAMPLE 11

The experiment is carried out as in Example 1, startingwith2-(2-chloroethyl)naphtho[1,8-cd]isothiazole 1,1-dioxide (6.5 g), triethylamine (3.4 cc) and 4-phenyl1,2,3,6,-tetrahydropyridine (3.9 g) in toluene (150 cc). The mixture is heated for 9 hours at boiling point, then cooled to a temperature of about 20° C. After purification by flash-chromatography on a silica column, under a current of argon at medium pressure (0.5–1.5 bar) with dichloromethane as eluant, and recrystallization from boiling acetonitrile (10 cc), 2-[2-(4-phenyl-1,2,3,6-tetrahydro-1-pyridyl)ethyl]naphtho[18-cd ]isothiazole 1,1-dioxide (2.5 g) is obtained, m.p. 106° C.

2-(2-Chloroethyl)naphtho[1,8-cd]isothiazole 1,1-dioxide may be prepared in the following manner: the experiment is carried out as in Example 1 for the preparation of 2-(3-chloropropyl)naphtho[1,8-cd]isothiazole 1,1-dioxide, starting with sodium hydride (4..8 g) in a 50% dispersion in vaseline oil, 1-bromo-2-chloroethane (8.8 cc) and 1,8-naphthosultom (20.5 g) in dimethylformamide (250 cc). After purification by flash-chromatography on a silica column, under a current of argon at medium pressure (0.5–1.5 bar) with a mixture of dichloromethane and cyclohexane (70–30 vol) as eluant, 2-(2-chloroethyl)naphtho [1,8-cd]isothiazole 1,1-dioxide (20.7 g) is obtained, m.p. 96° C.

EXAMPLE 12

The experiment is carried out as in Example 1, starting with 2-(3-chloropropyl)naphtho[1,8-cd]isothiazole 1,1-dioxide (2.8 g), triethylamine (2.8 cc) and 4,4-diphenylpiperidine hydrochloride (2.7 g) in toluene (30 cc). The mixture is heated for 8 hours at boiling point, then cooled to a temperature of about 20° C. Stirring is continued for 7 hours at this temperature. After purification by flash-chromatography on a silica column, under a current of argon at medium pressure (0.5–1.5 bar) with ethyl acetate as eluant, and recrystallization from boiling acetonitrile (10 cc), 2-[3-(4,4-diphenyl-piperidino)propyl]naphtho[1,8-cd]isothiazole 1,1-dioxide (1.6 g) is obtained, m.p. 168° C.

4,4-Diphenylpiperidine hydrochloride may be prepared according to the method described in German Patent 2139084.

EXAMPLE 13

The experiment is carried out as in Example 1, starting with 2-(3-chloropropyl)naphtho[1,8-cd]isothiazole 1,1-dioxide (5.6 g), triethylamine (2.8 cc) and 4-(4-bromophenyl)piperazine (4.8 g) in toluene (60 cc). The mixture is heated for 8 hours at boiling point, then cooled to a temperature of about 20° C. Stirring is continued for 8 hours at this temperature. After purification by flash-chromatography on a silica column, under a current of argon at medium pressure (0.5–1.5 bar) with ethyl acetate as eluant, and recrystallization from boiling acetonitrile (40 cc), 2-{3-[4-(4-bromophenyl)-1-piperazinyl]propyl}naphtho[1,8-cd ]isothiazole 1,1-dioxide (4.3 g) is obtained, m.p. 149° C.

4-(4-Bromophenyl)piperazine dihydrochloride may be prepared according to the method described by D.K. YUNG, J. Med. Chem., 21, 1301 (1978).

EXAMPLE 14

The experiment is carried out as in Example 1, starting with 2-(2-chloroethyl)naphtho[1,8-cd]isothiazole 1,1-dioxide (6.7 g), triethylamine (3.5 cc), 4-(4-fluorobenzoyl)piperidine (5.2 g) and sodium iodide (3.7 g) in dimethylformamide (100 cc). The mixture is heated for 6 hours at boiling point, then cooled to a temperature of about 20° C. After purification by flash-chromatography on a silica column, under a current of argon at medium pressure (0.5–1.5 bar) with dichloromethane as eluant, and recrystallization from boiling acetonitrile (8 cc), 2-{2-[4-(4-fluorobenzoyl)peridino]ethyl}naphtho[1,8cd]isothiazole 1,1-dioxide (2.9 g) is obtained, m.p. 145° C.

EXAMPLE 15

The experiment is carried out as in Example 1, starting with 2-(3-chloropropyl)naphtho[1,8-cd]isothiazole 1,1-dioxide (9.3 g), triethylamine (4.6 cc) and 4-(3-indoyl)-1,2,3,6-tetrahydropyridine (6.5 g) in dimethylformamide (100 cc). The mixture is heated for 8 hours at boiling point, then cooled to a temperature of about 20° C. Stirring is continued for 7 hours at this temperature. After purification by flash-chromatography on a silica column, under a current of argon at medium pressure (0.5–1.5 bar) with ethyl acetate as eluant, 2.9 g of a yellow solid are obtained, which is purified by flash-chromatography. on a silica column, under a current of argon at medium pressure (0.5–1.5 bar) with a mixture of dichloromethane and methanol (90–10 vol) as eluant, and recrystallization from boiling acetonitrile. (40 cc) 2-{3-[4-(3-Indolyl)-1,2,3,6-tetrahydro-1-pyridyl]-propyl}naphtho[1,8-cd]isothiazole 1,1-dioxide (2.1 g) is obtained,.-m.p. 226° C.

4-(3-Indolyl)-1,2,3,6-tetrahyiropyridine may be prepared according to the method described by L. NEDELEC et al , Eur. J. Med. Chem., 22, 33 (1987).

EXAMPLE 16

The experiment is carried out as in Example 1, starting with2-(4-chlorobutyl)naphtho[1,8-cd]isothiazole 1,1-dioxide (10 g), triethylamine (4.8 cc) and 4-phenyl-1,2,3,6-tetrahydropyridine (5.4 g) in toluene (300 cc). The mixture is heated for 9 hours at boiling point, then cooled to a temperature of about 20° C. After purification by flash-chromatography on a silica column, under a current of argon at medium pressure (0.5–1.5 bar) with ethyl acetate as eluant, and recrystallization from boiling acetoritrile (10 cc), 2-[4-(4-phenyl-1,2,3,6-tetrahydro-1-pyridyl) butyl}naphtho[1,8-cd]isothiazole 1,1-dioxide (2.6 g) is obtained, m.p. 101° C.

2-(4-Chloro.butyl)naphtho[1,8-cd]isothiazole 1,1-dioxide may be obtained in the following manner: operating as in Example 1 for the preparation of 2-(3-chloropropyl)naphtho[1,8-cd]isothiazole 1,1-dioxide, starting with sodium hydride (4.8 g) in a 50% dispersion in vaseline oil, 1-bromo-4-chlorobutane (11.9 cc) and 1,8-naphthosultam (20.5 g) in dimethylformamide (250 cc). After purification by flash-chromatography on a silica column, under a current of argon at medium pressure (0.5–1.5 bar) with a mixture of dichloromethane and cyclohexanone (30–70 vol) as eluant, 2-(4-chlorobutyl)-naphtho[[1,8-cd]isothiazole 1,1-dioxide (24.6 g) is obtained in the form of a yellow oil which is used in the crude state in the subsequent syntheses.

EXAMPLE 17

The experiment is carried out as in Example 1, starting with 2-(3-chloropropyl)naphtho[1,8-cd]isothiazole 1,1-dioxide (3.9 g), triethylamine (1.9 cc), 4-[bis(4-fluorophenyl)methylene]piperidine (3.7 g) and sodium iodide (2.1 g) in toluene (150 cc). The mixture is heated for 6 hours at boiling point, then cooled to a temperature of about 20° C. After purification by flash-chromatography on a silica column., under a current of argon at medium pressure (0.5–1.5 bar) with dichloromethene as eluant, 2-(3-[bis(4-fluorophenyl)-4-methylenepiperidino]propyl}naphtho[1,8-cd]-isothiazole 1,1-dioxide (4.6 g) is obtained in the form of a brown oil which is converted to the hydrochloride, m.p. 137° C.

4-[bis(4-Fluorophenyl)methylene]piperidine may be prepared according to the method described in European Patent 110 435.

EXAMPLE 1

Dimethylformamide (20 cc) is added to sodium hydride (0.6 g) in an 80% dispersion in vaseline oil, under a current of argon. The suspension obtained is stirred, then a solution of 5-bromonaphtho[1,8-cd]isothiazole 1,1-dioxide (5.7 g) in dimethylformamide (30 cc) is poured in drop by drop, over 15 minutes, maintaining the temperature between 20° C. and 30° C. The reaction medium is stirred for 15 minutes at a temperature of about 20° C., then a solution of 1-(3-chloropropyl)-4-phenyl-1,2,3,6-tetrahydropyridine (4.7 g) in dimethylformamide (20 cc) is poured in drop by drop, over 10 minutes, at a temperature of about 20° C. The reaction medium is heated for 1 hour at 100° C., then cooled to a temperature of about 20° C. The reaction mixture is redissolved in distilled water (300 cc) and extracted with ethyl acetate (200 cc). After washing with distilled water (3 x 50 cc), the organic extract is dried over magnesium sulphate and concentrated to dryness at 40° C. under reduced pressure (20 mm Hg; 2.7 kPa). After recrystallization from boiling acetonitrile (110 cc) 5-bromo-2-[3-(4-phenyl-1,2,3,6-tetrahydro-1-pyridyl)-propyl]naphtho[1,8-cd]isothiazole 1,1-dioxide (5.3 g) is obtained, m.p. 138° C.

1-(3-Chloropropyl)-4-phenyl-1,2,3,6-tetrahydropyridine may be prepared in the following manner: 4-phenyl-1,2,3,6-tetrahydropyridine (41 g), 1-bromo-3-chloropropane (100 cc), potassium carbonate (140 g) and acetonitrile (600 cc) are stirred for 12 hours at a temperature of about 20° C. After filtration, the solution is concentrated to dryness at 40° C. under reduced pressure (20 mm Hg; 2.7 kPa) The residue is purified by chromatography on a silica column with a mixture of cyclohexane and ethyl acetate (60–40 vol) as eluant. 1-(3-Chloropropyl)-4-phenyl-1,2,3,6-tetrahydropyridine (48 g) is obtained in the form of an oil.

5-Bromonaphtho[1,8-cd]isothiazole 1,1-dioxide may be obtained according to the process described by A. MUSTAFA et al., Arch. Pharm., 298, 741, (1965).

EXAMPLE 19

5-Acetylamino-2-(3-chloropropyl)napthto[1,8-cd]isothiazole 1,1-dioxide (0.8 g), 4-phenyl-1,2,3,6-tetrahydropyridine (0.4 g), potassium carbonate (4 g) and acetonitrile (25 cc) are heated at boiling point for 20 hours. The reaction mixture is cooled to a temperature of about 20° C. The solution is filtered and then concentrated to dryness at 40° C. under reduced pressure (20 mm Hg; 2.7 kPa). The residue is purified by chromatography on a silica column with a mixture of ethyl acetate and methylene chloride (70–30 vol) as eluant, then recrystallized from boiling ethanol (20 cc). 5Acetylamino-2-[3-(4-phenyl 1,2,3,6-tetrahydro-1-pyridyl)-propyl]-naphtho[1,8-cd]isothiazole 1,1-dioxide (0.35 g) is obtained, m.p. 178° C.

5-Acetylamino-2-(3-chloropropyl)naphtho[1,8-cd]isothiazole 1,1-dioxide may be prepared in the following manner: 5-amino-2-(3-chloropropyl)naphtho[1,8-cd]isothiazole 1,1-dioxide (2.1 g), sodium acetate (0.2 g) and acetic anhydride (15 cc) are heated at boiling point for 30 minutes. The reaction mixture is cooled to a temperature of about 20° C., treated with distilled water (5 cc) and heated at boiling point for 15 minutes. The mixture is cooled to a temperature of about 20° C., then concentrated to dryness at 50° C. under reduced pressure (0.5 mm Hg; 0.07 kPa). The residue is redissolved in dichloromethane (100 cc) and the solution is washed with distilled water (40 cc), dried over magnesium sulphate, then concentrated to dryness at 20° C under reduced pressure (20 mm Hg; 2.7 kPa). After recrystallization from boiling chloroform (15 cc), 5-acetylamino-2-(3-chloropropyl)naphtho[1,8-cd]isothiazole 1,1-dioxide (0.6 g) is obtained, m.p. 205° C.

5-Amino-2-(3-chloropropyl)naphtho[1,8-cd]isothiazole 1,1-dioxide may be prepared in the following manner: sodium borohydride (3.8 g) is added in small quantities, over one hour, to a solution of 5-nitro-2-(3-chloropropyl)naphtho[1,8-cd]isothiazole 1,1-dioxide (12.2 g) and nickel chloride with 6 water molecules (18 g) in methanol (600 cc), at a temperature of about 0° C. The reaction mixture is stirred for one hour at this temperature, then concentrated to dryness at 40° C. under reduced pressure (20 mm Hg; 2.7 kPa). The residue is redissolved in 1 N hydrochloric acid (50 cc), then treated with a 3 N ammonia solution (100 cc). The mixture is extracted with dichloromethane (500 cc). The organic extract is dried over magnesium sulphate and concentrated to dryness at 20° C. under reduced pressure (20 mm Hg; 2.7 kPa). The residue is purified by chromatography on a silica column with dichloromethane as eluant. 5-Amino-2-(3-chloropropyl)naphtho[1,8-cd]isothiazole 1,1-dioxide (3.4 g) is obtained in the form of an oil.

5-Nitro-2-(3-chloropropyl)naphtho[1,8-cd]isothiazole 1,1-dioxide may be prepared in the following manner: 2-(3-chloropropyl)naphtho[1,8-cd]isothiazole 1,1-dioxide (12 g), obtained as in Example 1, is added, over 5 minutes, to a 66.97% solution of nitric acid (d=1.4) (50 cc), at a temperature of about 0° C. The reaction mixture is stirred for one hour at this temperature, then treated with distilled water (150 cc) and stirred for a further 15 minutes. The precipitate is filtered, washed with distilled water (3 x 50 cc) then dried in air. 5-Nitro-2-(3-chloropropyl)naphtho[1,8-cd]isothiazole (12.2 g) is obtained and used in the crude state in the subsequent syntheses.

EXAMPLE 20

The experiment is carried out as in Example 18, starting with 5-chloronaphtho[1,8-cd]isothiazole 1,1-dioxide (1.2 g), sodium hydride (0.15 g) in an 80% dispersion in vaseline oil, 1-(3-chloropropyl)-4-phenyl-1,2,3,6-tetrahydropyridine (1.4 g), obtained as in Example 18, and dimethylformamide (30 cc). The reaction mixture is heated for one hour at 70° C., cooled to a temperature of about 20° C. then concentrated to dryness at 20° C. under reduced pressure (0.5 mm Hg; 0.07 kPa). The residue is redissolved in dichloromethane (100 cc) and the solution is washed with distilled water (50 cc), dried over magnesium sulphate and concentrated to dryness at 20° C. under reduced pressure (20 mm Hg; 2.7 kPa). The residue is purified by chromatography on a silica column with a mixture of dichloromethane and ethyl acetate (90–10 vol) as eluant, and recrystallized from boiling acetonitrile (30 cc). 5-Chloro-2-[3-(4-phenyl-1,2,3,6-tetrahydro-1-pyridyl)propyl]naphtho[1,8 cd]iso-
thiazole 1,1-dioxide (1 g) is obtained, m.p. 135° C.

5-Chloronaphtho[1,8-cd]isothiazole 1,1-dioxide may be obtained according to the process described by A. MUSTAFA et al., Arch. Pharm., 298, 741, (1965).

5-Chloro-2-[3-(4-phenyl-1,2,3,6-tetrahydro-1pyridyl)propyl]naphtho[1,8-cd]isothiazole 1,1-dioxide may also be prepared in the following manner: the experiment is carried out as in Example 19, starting with 5-chloro-2-(3-chloropropyl) naphtho[1,8-cd]isothiazole 1,1-dioxide (3.2 g), 4-phenyl-1,2,3,6-tetrahydropyridine (1.8 g), potassium carbonate (12 and acetonitrile (125 cc). The reaction mixture is heated at boiling point for 5 hours, then cooled to a temperature of about 20° C. After filtration and concentration to dryness at 40° C. under reduced pressure (20 mm Hg; 2.7 kPa), the residue is purified by chromatography on a silica column with a mixture of dichloromethane and ethyl acetate (85-15 vol) as eluant, and recrystallized from boiling acetonitrile (40 cc). 5-Chloro-2-[3-(4-phenyl-1,2,3,6-tetrahydro 1-pyridyl)propyl]naphtho[1,8-cd]isothiazole 1,1-dioxide (2.8 g) is obtained, m.p. 135° C.

5-Chloro-2-(3-chloropropyl)naphtho[1,8-cd]isothiazole 1,1-dioxide may be obtained in the following manner: a solution of chlorine (5.4 g) in acetic acid (100 cc) is poured drop by drop, over 15 minutes, into a solution of 2-(3-chloropropyl)naphtho[1,8-cd]isothiazole 1,1-dioxide (18 g), obtained as in Example 1, in acetic acid (200 cc) at a temperature of about 0° C. The reaction mixture is stirred for 24 hours at a temperature of about 20° C., then concentrated to dryness at 60° under reduced pressure (20 mm Hg; 2.7 kPa). The residue is purified by chromatography on a silica column with a mixture of dichloromethane and cyclohexane (50-50 vol) as eluant. 3,5Dichloro-2-(3-chloropropyl)-naphtho[1,8-cd]isothiazole 1,1-dioxide (1.7 g), m.p. 164° C, and 5-chloro-2-(3chloropropyl)naphtho[1,8-cd]isothiazole 1,1-dioxide (3.2 g), m.p. 80° C., are obtained.

EXAMPLE 21

The experiment is carried out as in Example 19, starting with 3,5-dichloro-2-(3-chloropropyl)naphtho[1,8-cd]isothiazole 1,1-dioxide (1.7 g) obtained as in Example 20, 4-phenyl-1,2,3,6-tetrahydropyridine (0.85 g), potassium carbonate (7 g) and acetonitrile (90 cc). The reaction mixture is heated at boiling point for 20 hours, then cooled to a temperature of about 20° C. The solution is filtered and then concentrated to dryness at 40° C. under reduced pressure (20 mm Hg; 2.7 kPa). The residue is recrystallized from boiling acetonitrile (25 -cc) 3,5-Dichloro-2-[3-(4-phenyl-1,2,3,6-tetra hydro-1-pyridyl)propyl]naphtho[1,8-cd]isothiazole 1,1-dioxide (1 g) is obtained, m.p. 126° C.

EXAMPLE 22

The experiment is carried out as in Example 18, starting with 6-chloronaphtho[1,8-cd]isothiazole 1,1-dioxide (1.4 g), 1-(3-chloropropyl)-4-(4-fluorophenyl) piperazine (1.5 g), sodium hydride (0.18 g) in an 80dispersion in vaseline oil and dimethylformamide (15 cc). The reaction mixture is heated for 1 hour 30 minutes at 90° C., cooled to a temperature of about 20° C. and then concentrated to dryness at 60° C. under reduced pressure (0.5 mm Hg; 0.07 kPa). The residue is redissolved in dichloromethane (50 cc) and the solution is washed with distilled water (20 cc), dried over magnesium sulphate and concentrated to dryness at 20° C. under reduced pressure (20 mm Hg; 2.7 kPa). The residue is purified by chromatography on a silica column with a mixture of dichloromethane and ethyl acetate (95-5 vol) as eluant, then recrystallized from boiling acetonitrile (10 cc). 6-Chloro-2-{3-[4-(4-fluorophenyl)-1-piperazinyl]propyl}-naphtho[1,8-cd]isothiazole 1,1-dioxide (1.2 g) is obtained, m.p. 125° C.

6-Chloronaphtho[1,8-cd]isothiazole 1,1-dioxide may be prepared in the following manner: 8-amino-4-chloro-1-naphthalenesulfonic acid (13.3 g) and phosphorus oxychloride (30 cc) are heated at boiling point for 3 hours. The reaction mixture is then cooled to a temperature of about 0° C., and then treated with distilled water (100 cc). The precipitate is isolated by filtration, washed with distilled water (3×20 cc) and extracted with chloroform (3×150 cc). The organic extracts are dried over magnesium sulphate and concentrated to dryness at 40° C. under reduced pressure (20 mm Hg; 2.7 kPa). Crude 6-chloronaphtho[1,8-cd]isothiazole 1,1-dioxide (1.4 g) is obtained, which is used as such in the subsequent syntheses.

8-Amino-4-chloro-1-naphthalenesulphonic acid may be prepared according to the process described by P. FRIEDLANDER et al., Chem. Ber., 55B, 45, (1922).

1-(3-Chloropropyl)-4-(4-fluorophenyl)piperazine may be prepared in the following manner: the experiment is carried out as in Example 18 for 1-(3-chloropropyl)-4-phenyl-1,2,3,6-tetrahydropyridine, starting with 1-(4fluorophenyl)piperazine (50 g), 1-bromo-3-chloropropane (68 cc), sodium carbonate (97 g) and acetonitrile (400 cc). The reaction mixture is stirred for 12 hours at a temperature of about 20° C. and the solution is filtered and then concentrated to dryness at 40° C. under reduced pressure (20 mm Hg; 2.7 kPa). The residue is purified by chromatography on a silica column with ethyl acetate as eluant. 1-(3-Chloropropyl)-4-(4-fluorophenyl)piperazine (44.4 g) is obtained in the form of an oil.

EXAMPLE 23

A solution of 1-(3-chloropropyl)-4-pheny-1,2,3,6-tetrahydropyridine (4.9 g) in dimethylformamide (20 cc) is added to a solution of the sodium salt of 2H-isothiazolo[3,4,5-de]isoquinoline 1,1-dioxide (obtained by heating, after the evolution of gas has ceased, a solution of 4-bromo-5-isoquinolylsulphonamide (4.1 g) in dimethylformamide (25 cc) and a suspension of sodium hydride (0.85 g) in an 80% dispersion in vaseline oil in dimethylformamide (50 cc) at 110° C. for 2 hours and 30 minutes) cooled to 20° C. The reaction medium is heated for 2 hours at 100° C., then poured into a mixture of water (300 cc) and ethyl acetate (300 cc). The organic phase is washed with water (3×300 cc), dried over magnesium sulphate and concentrated to dryness. The residue is purified by chromatography on a silica column under a slight overpressure of nitrogen, eluting with ethyl acetate and then with a mixture of ethyl acetate and ethanol (95-5 vol). 2-[3-(4-Phenyl-1,2,3,6-tetrahydropyridyl)propyl-2H-isothiazolo[3,4,5-de ]isoquinoline 1,1-dioxid®(1.4 g) is obtained in the form of a yellow oil. 1.8 g of this product are purified with a second similar chromatography stage to give 2-[3-(4-phenyl-1,2,3,6-tetrahydropyridyl)propyl]-2H-isothiazolo[3,4,5-de]isoquinoline 1,1-dioxide (1.6 g) (Rf =0.27; support: silica gel; eluant: ethyl acetate-ethanol (9-1 vol)). This product is dissolved in ethyl acetate (100 cc) before adding a 3 N solution of hydrochloric acid in isopropyl oxide (5 cc). The precipitate is centrifuged, washed with ethyl acetate and dried under vacuum (0.1 Hg) at 35° C. 2-[3-(4-Phenyl-1,2,3,6-tetrahydropyridyl,-propyl]-2H-isothiazolo[3,4,5-de]isoquinoline 1,1-dioxide dihydrochloride (1.6 g) is obtained in the form of a yellow (amorphous) solid.

4Bromo-5-isoquinolylsulphonamide may be obtained in the following manner: ammonia is bubbled into dry tetrahydrofuran at −50° C. until saturation. This solution is treated with a suspensiOn Of 4-bromo-5-isoquinolylsuiphonyl chloride (8 g) in tetrahydrofuran (50 cc). The reaction mixture is left to return progressively to 20° C. The precipitate formed is centrifuged, washed with tetrahydrofuran (3×10 cc), water (3×30 cc) and ethyl acetate (2×10 cc), then centrifuged and dried. 4-Bromo5-isoquinolylsulphonamide (4.5 g) is obtained in the form of a beige solid the m.p. of which is greater than 270° C.

4-Bromo-5-isoquinolylsulphonyl chloride may be obtained by the following process: a solution of 5-amino4-bromoisoquinoline 4-bromoisoquinoline (4.46 g) in concentrated hydrochloric acid (d=1.19) (44 cc) is cooled to −5° C. then is treated with a solution of sodium nitrite (1.93 g) in water (10 cc). The reaction mixture is stirred for 1 hour at 0° C. The solution obtained is poured into a saturated solution of sulphur dioxide in acetic acid (48 ml), to which has been added a solution of cuprous chloride (0.65 g) in water (5.6 cc). The reaction mixture is stirred until the evolution of gas has finished, and then 10 is extracted with dichloromethane (2×100 cc). The organic phases are pooled, washed with water, dried over magnesium sulphate and concentrated. 4-Bromo-5-isoquin--lylsulphonyl chloride (5.6 g) is obtained in the form of a yellow solid which is used as such in the subsequent syntheses.

5-Amino-4-bromoisoquinoline may be prepared in the following manner: a suspension of 4-bromo-5-nitroisoquinoline (25.3 g) in 2 N hydrochloric acid (180 cc) is progressively added to a solution of stannous chloride (90 g) in concentrated hydrochloric acid (d=1.19) (100 cc). The reaction mixture is heated under reflux for 90 minutes, then is cooled and poured into a 2 N caustic soda solution (2 1), stirring and cooling to 0° C. The precipitate is washed with water, centrifuged and dried 5-Amino-4-bromoisoquinoline (21.6 g) is obtained in the form of yellow crystals, m.p. 155° C. 4-Bromo-5-nitroisoquinoline may be obtained by the process described by M.D. NAIR et al., Indian J. Chem. Soc., 5, 224 (1967).

EXAMPLE 24

The experiment is carried out as in Example 1, starting with 2-(3-chloropropyl)naphtho[1,8-cd]isothiazole 1,1-dioxide (12 g), triethylamine (6 cc) and 4-(4-hydroxyphenyl)-1,2,3,6-tetrahydropyridine (7.5 g) in dimethylformamide (120 cc). The mixture is heated for 8 hours at boiling point, then cooled to a temperature of about 20° C. Stirring is continued for 12 hours at this temperature. After purification by flash-chromatography on a silica column, under a current of argon at medium pressure (0.5–1.5 bar) with ethyl acetate as eluant, and recrystallization from boiling acetonitrile (80 cc), 2-{3-[4-(4-hydroxyphenyl)-1,2,3,6-tetrahydro-1-pyridyl]propyl} naphtho[1,8-cd]isothiazole 1,1-dioxide (3.3 g) is obtained, m.p. 198° C.

4-(4-Hydroxyphenyl)-1,2,3,6-tetrahydropyridine may be prepared in the following manner: a 35% solution of hydrobromic acid in acetic acid (250 cc) is added, over 1 hour and at a temperature of about 5° C, to N-benzyloxycarbonyl4-hydroxy-4-(4-methoxyphenyl)piperidine (21 g). The mixture is stirred for 1 hour at a temperature of about 20° C., then the aqueous phase is washed with diethyl ether (3×500 cc). After decantation, the aqueous phase is redissolved in water (250 cc) and alkalinized with 10 N caustic soda to pH 10. After extraction with dichloromethane (4×500 cc), the precipitate formed is separated by filtration. 4-(4-Hydroxy phenyl)-1,2,3,6-tetrahydropyridine (7.5 g) is thus obtained, m.p. 245° C.

N-Benzyloxycarbonyl-4-hydroxy-4-(4-methoxyphenyl)piperidine may be prepared in the following manner: p-bromoanisole (1 cc) and a few crystals of iodine are added, at a temperature of about 20° C. and under a current of argon, to magnesium turnings (9.3 g) in diethyl ether (150 cc). After 5 minutes, the solvent in the reaction medium is under reflux and a solution of p-bromoanisole (24.7 cc) in diethyl ether (300 cc) is added over 1 hour in such a manner as to maintain the refluxing of the solvent. Stirring is continued for 30 minutes at this temperature then, after cooling the mixture to a temperature of about 20° C., a solution of N-benzyloxycarbonyl-4-piperidone (48.2 g) in ethyl ether (450 cc) is poured in. Stirring is continued for 15 hours at this temperature. The reaction medium is then hydrolysed with a saturated solution of ammonium chloride to pH 6-7, then extracted with diethyl ether (3×500 cc). The organic phase is dried over anhydrous magnesium sulphate and concentrated to dryness under reduced pressure (20 mm Hg; 2.7 kPa). The residual oil is purified by flash-chromatography on a silica column, under a current of argon at medium pressure (0.5–1.5 bar) with dichloromethane and then a mixture of dichloromethane and methanol (90-10 vol) as eluant. N-Benzyloxycarbonyl-4-hydroxy-4-(4-methoxyphenyl)-piperidine (21.2 g), m.p. 98° C., is thus obtained, which is used in the crude state in the subsequent syntheses.

N-Benzyloxycarbonyl-4-piperidone may be prepared according to the manner described by H. STETTER et al., Chem. Ber. 105, 2773 (1972).

EXAMPLE 25

The experiment is carried out as in Example 1, starting with 2-(3-chloropropyl)naphtho[1,8-cd]isothiazole 1,1-dioxide (6.74 g), triethylamine (3.4 cc) and 4-(4-methoxyphenyl)-1,2,3,6-tetrahydropyridine (4.5 g) in dimethylformamide (70 cc). The mixture is heated for 8 hours at boiling point, then cooled to a temperature of about 20° C. Stirring is continued for 12 hours at this temperature. After purification by flash-chromatography on silica gel, under a current of argon at medium pressure (0.5-1.5 bar) with ethyl acetate as eluant, and recrystallization from boiling acetonitrile (60 cc), 2{3-[4-(4-methoxyphenyl)-1,2,3,6-tetrahydro -1-pyridyl]-propyl}naphtho[1,8-cd]isothiazole 1,1-dioxide (2 g) is obtained, m.p. 178° C.

EXAMPLE 26

The experiment is carried out as in Example 1, starting with 2-(3-chloropropyl)naphtho[1,8-cd]isothiazole 1,1-dioxide (75 g), triethylamine (37.5 cc) and 4-(4-nitrophenyl)poperazine (55.3 cc) in toluene (600 cc). The mixture is heated for 10 hours at boiling point, then cooled to a temperature of about 20° C. After purification by flash-chromatography on a silica column, under a current of argon at medium pressure (0.5-1.5 bar) with a mixture of dichloromethane and ethyl acetate as eluant (80-20 vol), and recrystallization from boiling methyl ethyl ketone (1100 cc), 2-(3-[4-(4-nitrophenyl)-1-piperazinyl]propyl}naphtho[1,8-cd]isothiazole 1,1-dioxide(41.8 g) is obtained, m.p. 186° C.

EXAMPLE 27

2-{3-[4-(4-Nitrophenyl)-1-piperazinyl]propyl}-naphtho[1,8-cd]isothiazole 1,1-dioxide (30 g), stannous chloride dihydrate (74.8 g) and ethanol (500 cc) are heated for one hour at 60° C. under a current of argon. Then sodium borohydride (1.3 g) is added over one hour in small portions. Stirring is continued for one hour at 60° C., then for 15 hours at a temperature of about 20° C. The mixture is poured into water and ice (500 cc) then alkalinized with 4 N caustic soda to pH 9. The organic phase is extracted with diethyl ether (4×200 cc), absorbed in charcoal 3S (3 g), dried on anhydrous magnesium sulphate, filtered and concentrated to dryness under reduced pressure (200 mm Hg; 2.7 kPa). The residue obtained in purified by recrystallization, first from boiling 1-propanol (250 cc), then twice from boiling ethanol (20 cc). 2-{3-[4-(4-Aminophenyl)-1-piperazinyl]propyl}naphthol1,8-cd]isothiazole 1,1-dioxide (2.4 g) is thus obtained, mp. 113° C.

EXAMPLE 28

The experiment is carried out as in Example 1, starting with 2(3-chloropropyl)naphtho[1,8-cd]isothiazole 1,1-dioxide(8.4 g), triethylamine (4.2 cc) and 4-(3-fluorophenyl)piperazine (5.3 g) in toluene (100 cc). The mixture is heated for 8 hours at boiling point, then cooled to a temperature of about 20° C. After purification by flash-chromatography on a silica column, under a current of argon at medium pressure (0.5-1.5 bar) with dichloromethane and then a mixture of dichloromethane and ethyl acetate (5-50 vol) as eluant, and recrystallization from boiling acetonitrile (20 cc), 2-(3-[4-(3-fluorophenyl)-1-piperazinyl]propyl}naphtho[1,8cd]isothiazole 1,1-dioxide (4.7 g) is obtained, m.p. 103° C.

4-(3-Fluorophenyl)piperazine may be prepared according to the method described by L. THUNUS et al., Ann. Pharm., 38,353 (1980).

EXAMPLE 29

The experiment is carried out as in Example 1, starting with 2(3-chloropropyl)naphtho[1,8-cd]isothiazole 1,1-dioxide(7 g), triethylamine (3.5 cc) and 4-(2-fluorophenyl)piperazine (4.4 g) in toluene (150 cc). The mixture is heated for 8 hours at boiling point, then cooled to a temperature of about 20° C. After purification by flash-chromatography on a silica column, under a current of argonat medium pressure (0.5-1.5 bar) with dichloromethane is eluant, and recrystallization from boiling acetonitrile (15 cc), 2-{3-[4-(2-fluorophenyl)1-piperazinyl]propyl}naptho[1,8]isothiazole 1,1dioxide (4.8 g) is obtained, m.p. 112° C.

4-(2-Fluorophenyl)piperazine may be prepared according to the method described by L. THUNUS et al., Ann. Pharm., 38, 53 (1980).

EXAMPLE 30

The experiment is carried out as in Example 1, starting with 2-3-chloropropyl)naphtho[1,8-cd]isothiazole 1,1-dioxide 7 g), triethylamine (3.5 cc) and 4-(4-methylphenyl)piperazine (4.4 g) in toluene (100 cc). The mixture is heated for 6 hours at boiling point, then cooled to a temperature of about 20° C. After purification, flash-chrotography on a silica column, under a current of argon at medium pressure (0.5-1.5 bar) with a mixture of dichlopomethane and ethyl acetate (80-20 vol) as eluant, and recrystallization from boiling acetonitrile (40 cc), 2(3-[4-(4-methylphenyl)-1-piperaz-inylpropyl)-naphtho[1,8-cd]isothiazole 1,1-dioxide (4.5 g) is obtained, m.p. 13° C.

4-(4-Methylphenyl)piperazine may be preparedaccording to the1method described by L. THUNUS et al., Ann. Pharm., 38, 53 (1980).

EXAMPLE 31

The experiment is carried out as in Example 1, starting with 2-(3-chloropropyl)naphtho[1,8-cd]isothiazole !,1-dioxide (7.2 g), triethylamine (3.6 cc) and 1-(4-piperidinyl)-2-benzimidazolinone (5.6 g) in dimethylformamide (100 cc). The mixture is heated for 8 hours at boiling point, then cooled to a temperature of about 20° C. After purification by flash-chromatography on a silica column, under a current of argon at medium pressure (0.5-1.5 bar) with a mixture of dichloromethane and ethanol (95-5 vol) as eluant, and recrystallization from boiling acetonitrile (200 cc), 2-{3-[4-(2-oxyl-benzimidazolinyl )piperidino]propyl}naphtho[1,8-cd]isothiazole 1,1-dioxide (1.6 g) is obtained, m.p. 253° C.

1-(4-Piperidinyl)-2-benzimidazolinone may be prepared according to the method described in U.S. Pat. No. 4,470,989.

EXAMPLE 32

The experiment is carried out as in Example 1, starting with 2-(3-chloropropyl)naphtho[1,8-cd]isothiazole 1,1-dioxide (3.6 g), triethylamine (1.8 cc) and 4(1,2-benzisoxazol-3-yl)piperazine (2.69) in dimethylformamide (200 cc). The mixture is heated for 8 hours at boiling point, then cooled to a temperature of about 20° C. After purification by flash-chromatography on silica gel, under a current of argon at medium pressure (0.5-1.5 bar) with dichloromethane as eluant, and recrystallization from boiling acetonitrile (30 cc), 2-{3-[4-(1,2-benzisoxazol-3-yl) -1-piperazinylpropyl}naphtho[1,8-cd]isothiazole 1,1-dioxide (1.4 g) is obtained, m.p. 263° C.

4-(1,2-Benzisoxazol-3-yl)piperazine may be prepared according to the method described by J.P. YEVICH et al., J. Med. Chem., 39, 359 (1986).

EXAMPLE 33

The experiment is carried out as in Example 1, starting with 2-(2-chloroethyl)naphtho[1,8-cd]isothiazole 1,1-dioxide (5.3 g), triethylamine (3 cc) and 4-(1,2-benzisoxazol-3-yl)piperazine (4 g) and sodium iodide (3 g) in dimethylformamide (60 cc). The mixture is heated for 8 hours at boiling point, then cooled to a temperature of about 20° C. After purification by flash-chromatography on silica gel, under a current of argon at medium pressure (0.5-1.5 bar) with ethyl acetate as eluant, and recrystallization from boiling acetonitrile (22 cc), 2-{2-[4-(1,2-benzisoxazol-3-yl)-1-piperazinyl]ethyl}naphtho[1,8-cd]isothiazole 1,1-dioxide (2.3 g) is obtained, m.p. 148° C.

EXAMPLE 34

The experiment is carried out as in Example 1, starting with2-(4-chlorobutyl)naphtho[1,8-cd]isothiazole 1,1-dioxide (5.8 g), triethylamine (3 cc) and 4-(1,2-benzisoxazol-3-yl)piperazine (4 g) in dimethylformamide (55 cc). The mixture is heated for 8 hours at boiling point, then cooled to a temperature of about 20° C. After purification by flash-chromatography on a silica column, under a current of argon at medium pressure (0.5-1.5 bar) with ethyl acetate as eluant, and recrystallization from boiling acetonitrile (15 cc), 2-{4-[4-(1,2-benzisoxazol-3-yl)-1-piperazinyl]butyl}napto 1,8-cd]isothiazole 1,1dioxide (2.2 g) is obtained, m.p. 138° C.

EXAMPLE 35

The experiment is carried out as in Example 1, starting with 2-(3-chloropropyl)naphtho[1,8-cd]isothiazole 1,1-dioxide (11 g), triethylamine (11 cc) and 41,2-benzisothiazole-3-yl)piperazine (8.6 g) in dimethylfomamide (120 cc). The mixture is heated for 8 hours at boiling point, then cooled. to a temperature of about 20° C. After purification by flash-chromatography on a silica column, under a current of argon at medium pressure with ethyl acetate as eluant, and recrystallization from boiling methyl ethyl ketone (160 cc), 2-{3-[4-(1,2-benzisothiazole-3-yl)-1-piperazinyl]propyl}napthto[1,8-cd}isothiazole 1,1-dioxide (4.4 g) is obtained, m.p. 172°-173° C.

EXAMPLE 36

The experiment is carried out as in Example 1, startingwith2-(2-chloroethyl)naphtho[1,8-cd]isothiazole 1,1-dioxide (8.9 g), triethylamine (4.5 cc) and 4-(1,2-benzisothiazole-3-yl)piperazine (6.6 g) in dimethylformamide (95 cc). The mixture is heated for 8 hours at boiling point, then cooled to a temperature of about 20° C. After purification by flash-chromatography on a silica column, under a current of argon at medium pressure (0.5-1.5 bar) with ethyl acetate as eluant, and recrystallization from boiling acetonitrile (90 cc), 2-{2-[4-(1,2-benziso-thiazol-3-yl)-1-piperazinyl]ethyl}-naphtho[1,8-cd]isothiazole 1,1-dioxide (4.6 g) is obtained, m.p. 162°.

EXAMPLE 37

The experiment is carried out as in Example 1, starting with2-(4-chlorobutyl)naphtho[1,8-cd]isothiazole 1,1-dioxide (8.9 g), triethylamine (4.5 cc) and.4-(1,2-benzisothiazole-3-yl)piperazine (6.6 g) in dimethylformamide (95 cc). The mixture is heated for 8 hours at boiling point, then cooled to a temperature of about 20° C. After purification by flash-chromatography on a silica column, under a current of argor at medium pressure (0.5-1.5 bar) with ethyl acetate as eluant, and recrystallization from boiling acetonitrile (30 cc), 2{4-[4-(1,2-benzisothiazole-3-yl)·1-piperazinyl]butyl}-naphtho[1,8]isothiazole 1,1-dioxide (6.3 g) is obtained, m.p. 123° C.

EXAMPLE 38

The experiment is carried out as in Example 1, starting with2-(4-chlorobutyl)naphtho[1,8-cd]isothiazole 1,1-dioxide (8.9 g), triethylamine (4.3 cc) and 4-(4-chlorophenyl)-1,2,3,6-tetrahydropyridine (5.8 g) in toluene (80 cc). The mixture is heated for 8 hours at boiling point, then cooled to a temperature of about 20° C. Stirring is maintained for 8 hours at this temperature. After purification by flash-chromatography on a silica column, under a current of argon at medium pressure (0.5-1.5 bal) with ethyl acetate as eluant, and recrystallization from boiling acetonitrile (25 cc), 2{4-[4-(4-chlorophenyl)1,2,3,6-tetrahydro -1-pyridyl]butyl}naphtho[1,8cd]isothiazole 1,1-dioxide (4.1 g) is obtained, m.p. 12° C.

EXAMPLE 39

The experiment is carried out as in Example 1, starting with 2-(chloropropyl)naphtho[1,8-cd]isothiazole 1,1-dioxide (1.2 g), triethylamine (16.8 cc) and 4-(3-hydroxyphenyl)piperazine dihydrobromide (13.6 g) in dimethylformamide (250 cc). The mixture is heated for 6 hours at boiling point, then cooled to a temperature of about 20° C. Stirring is maintained for 6 hours at this temperature. After purification by crystallization from isopropyl oxide 30 cc), then recrystallization from boiling acetonitrile (125 cc), 2-}3-4-(3-hydroxyphenyl)-1-piperazinyl]propyl }naphtho[1,8-cd]isothiazole 1,1-dioxide (4.6 g) isobtained, m.p. 175° C.

4-(3-Hydrohyphenyl)piperazine dihydrobromide may be prepared in the following manner: the experiment is carried out as in Example 8 for the preparation of 4-(4hydroxyphenyl)piperazine dihydrobromide, starting with 4-(3-methoxyphenylpiperazine (25 g) and a 47% aqueous solution of hydropromic acid (360 cc). The mixture is heated at boilingpoint for 2 hours, then cooled to a temperature of about 20° C. Stirring is maintained for 15 hours at this temperature, then the mixture is concentrated at 40° C. under reduced pressure (20 mm Hg; 2.7 kPa). The residual oil is redissolved in acetonitrile (100 cc); The precipitate formed is separated by filtration, washed with acetonitrile (2×50 cc) and isopropyl oxide (2 x 50 cc). 4-(3-Hydroxyophenyl)piperazine dihydrobromide (m.p.: 240° C.) (42.5 g) is obtained, which is used in the crude state in the subsequent syntheses.

EXAMPLE 40

The experiment is carried out as in Example 1, starting with 2-(chloropropyl)naphtho[1,8-cd]isothiazole 1,1-dioxide (02 9), triethylamine (10.5 cc) and 4-(2-hydroxyphenyl)piperazine dihydrobromide (8.5 9) in dimethylformamide (150 cc). The mixture is heated.for 6 hours at boiling point, then cooled to a temperature of about 20° C. Stirring is maintained for 15 hours at this temperature. After purification by flash-chromatography on a silica column, under a current of argon at medium pressure (0.5-1.5 ) with a mixture of dichloromethane and ethyl acetate(50-50 vol) as eluant, and recrystallization lization from acetonitrile (25 cc), 2-{3-

[4-(2-hydroxyphenyl)-1-piperazinyl]propyl}naphtho[1,8-cd]isothiazole 1,1-dioxide (5.8) is-obtained, m.p. 128° C.

4-(=- l)piperazine dihydrobromide may be prepared in the following manner: the experiment is carried out as in Example 8 for the preparation of 4-(4hydroxyphenyl)piperazine dihydrobromide, starting with 4-(2-methoxypheny)piperazine (25 g) and 47% aqueous solution of hydrdromic acid (360 cc). The mixture is heated at boiling point for 9 hours, the cooled to a temperature close to 20° C. Stirring is maintained for 15 hours at this temperature, then the mixture is concentrated at 40° C underreduced pressure (20 mm g; 2.7 kPa). The residual oil is redissolved in acetonitrile (40 cc) and isopropyl oxide (40 cc); the precipitate formed is separated by filtration, washed with oxide (2×50 cc). 4-(2-Hydroxyphenyl)piperazine dihydrobromide (m.p.: 235° C.) (18g) is obtained, which is used in the crude state in the subsequent syntheses.

EXAMPLE 41

The experiment is carried out as in Example 1, starting with2-(2-chloroethyl)naphtho[1,8]isothiazole 1,1-dioxide (10.6g), triethylamine (5.6cc), sodium iodide (6 g) and 4-3-indolyl)-1,2,3,6-tetraopyridine (8.0 g) in dimetylformamide (200 cc). The mixture is heated for 8 house at boiling point, the cooled to a temperature of about 20° C. Stirring is continued for 2 hours at this temperature. After purification by crystallization from acetenitrile (150 cc) and recrystallization from boiling methyl ethyl ketone (150 cc), 2-{2-[4-(3-indolyl)-1,2,3,6-tetrahydro-1-pyridyl] ethyl}napthho[1,8-cd]isothiazole 1,-dioxide (0.8 g) is obtained, m.p. 208° C.

EXAMPLE 42

The experiment is carried out as in Example 1, starting with2-(4-chlorobutyl)naphtho[1,8-isothiazole 1,1-dioxide (2.95g), sodium bicarbonate (0.84 g) and 4(3-indolyl)-1,2,3,6-tetrahydropyridine (1.98 g) in a formamide (50 cc) and tetrahydrofuran mixture of dimethylformamide (50 cc) and tetrahydrafuran (50 cc). The mixture is heated for 4 hours at boiling point, then cooled to a temperature of1 about 20° C. Stirring is maintained for 2 hours at this 1 temperature. After purificatiod by crystallization from 1methyl ethyl ketone (15 cc) by flash-chromatography on a silica column, under a current of argon at medium pressure (0.5–1.5 bar) with dichloromethane and then ethyl acetate as eluant, and recrystallization from boiling methyl ethyl ketone (65 cc), 2-{4-[4-(3-indolyl)-1,2,3,6-tetrahydrol-pyridyl]butyl}napthho [1,8-cd]isothiazole1 1,1-dioxide (1.5 g) is obtained, m.p. 203° C.

EXAMPLE 43

The experiment is carried out as in Example 1, starting with 2-3-chloropropyl)naphtho[1,-cd]isothiazole 1,1-dioxide 2.81 g), triethylamine (1.4 cc) and 4(4-chlorophenyl)pperidine (1.96 g) in toluene (30 cc). The mixture is heated for 8 hours at boiling point, then cooled to a temperature of about 20° C. Stirring is continued for 8 hours at this temperature. Afer purification by flash-chromatography on a silica column, under a current of argon at medium pressure (0.5–1.5 bar) with ethyl acetate as eluant, and recrystallation firstly from boiling acetonitrile (12 cc) and then from boiling acetonitrile (17 cc), 2-{3-[4-(4-chlorophenyl)-piperidino ]propyl}napthho[1,8-cd]isothiazole 1,1-dioxide (1.4 g) is obtained, m.p. 111° C.

4-(4-Chlorophenyl)piperdine may be prepared according to the method described by L. GOOTJES et al., Arzneim. Forsch., 17, 1145 (1967).

EXAMPLE 44

A mixture of 2-{3-[4-(3-indolyl)-1,2,3,6-tetrahydro-1-pyridyl]propyl}naphtho [1,8-cd]isothiazole 1,1-dioxide (11 g) in dmethylformamide (150 cc) is added over 30 minutes to sodium hydride (1.3 g) in a 50% dispersion in vaseline oil, under a current of argon, maintaining the temperature at about 20° C. The reaction medium is stirred for 2 hours at a temperature of about 20° C. then a solution of methyl iodide (3.9 g) in dioxane (50 cc) is added over 15 minutes. Stirring is maintained for 15 hours at a temperature of about 20° C. The reaction mixture is redissolved in distilled water (250 cc) and the organic phase is extracted with dichloromethane (4×100 cc) and then washed with distilled water (400 cc), dried over anhydrous magnesium sulphate, filtered and concentrated to dryness at 40° C. under reduced pressure (20 mm Hg; 2.7 kPa). The residue obtained is purified by flash-chromatography on a silica column, under a current of argon at medium pressure (0.5-1.5 bar) with dichloromethane as eluant, and recrystallized from boiling methyl ethyl ketone (70 cc). 2-{3-[4-(1-Methyl-3-indolyl)1,2,3,6-tetrahydro-1-pyridyl]propyl }naphtho[1,8-cd]isothiazole 1,1-dioxide (3.3 g) is obtained, m.p. 161° C.

EXAMPLE 45

The experiment is carried out as in Example 44, starting with 2-{3-[4-(3-indolyl)-1,2,3,6-tetrahydro-1pyridyl]propyl}naphtho[1,8-cd]isothiazole 1,1-dioxide (11 g) in dimethylformamide (150 cc), acetyl chloride (1.95 cc) in dioxane (50 cc) and sodium hydride (1.3 g as a 50% dispersion in vaseline oil). The mixture is stirred for 15 hours at a temperature of about 20° C. After purification by flash-chromatography on a silica column, under a current of argon at medium pressure (0.5–1.5 bar), firstly with dichloromethane as eluant and then with ethyl acetate as eluant, then recrystallization from boiling acetonitrile (45 cc), 2-{3-[4-(1-acetyl-3-indolyl)-1,2,36-tetrahydro-1-pyridyl]propyl}naphtho[1,8-cd]isothiazole 1,1-dioxide (1.3 g) is obtained, m.p. 163° C.

EXAMPLE 46

The experiment is carried out as in Example 1, starting with 2-(3-chloropropyl)naphtho[1,8-cd]isothiazole 1,1-dioxide (2,8 g), 4-hydroxy-4-(4-methylphenyl)-piperidine (2.1 g) and sodium bicarbonate (0.94 g) i mixture of dimethylformamide (60 cc) and tetrahydrofuran (50 cc). The mixture is heated for 5 hours at a temperature of about 100° C. then cooled to a temperature of about 20° C. Stirring is maintained for 15 hours at this temperature. After purification by flash-chromatography on a silica column, under a current of argon at medium pressure (0.5–1.5 bar) with a mixture of dichloromethane and methanol (95-5 vol) as eluant, 2-{3-[4-(4-methylphenyl)-4-hydroxypiperidino ]propyl} naphtho[1,8-cd]isothiazole 1,1-dioxide (1 g) is obtained, in the form of 1,1-dioxide (1 g) is obtained, in the form of the hydrochloride of m.p. 218° C.

4-Hydroxy-4-(4-methylphenyl)piperidine may be prepared in the following manner: 1-benzyl-4-hydroxy-4(4-methylphenyl)piperidine (5 g), 5% palladium-on-charcoal (1 g) and methanol (100 cc) are charged into a 250 cc bomb apparatus. The reaction medium is hydrogenated under pressure (52 bar) at 50° C. for 16 hours. After cooling to a temperature close to 20° C. and purging with nitrogen, the mixture is filtered through fritted glass and washed with methanol (3×50 cc). The filtrate is concentrated to dryness at 40° C. under reduced pressure (20 mm Hg; 2.7 kPa). 4-Hydroxy-4-(4-methylphenyl)piperidine (3.4 g) is obtained in the form of a brown oil, which is used in the crude state in the subsequent syntheses.

1-Benzyl-4-hydroxy-4-(4-methylphenyl)piperidine may be prepared in the following manner: several drops of p-bromotoluene and a crystal of iodine are added to magnesium turnings (1.7 g) in diethyl ether (25 cc), under a current of argon. The mixture is heated to boiling, then a solution of p-bromotoluene (12.1 g) in diethyl ether (70 cc) is poured in in such a manner as to maintain the reflux. The reaction medium is stirred for 30 minutes at the boiling point of the solvent, then cooled to a temperature of about 20° C. A solution of 1benzylpiperidone (6.7 g) in diethyl ether (60 cc) is added, and stirring is maintained for 15 hours at the same temperature. A saturated solution of ammonium chloride (150 cc) is added to the mixture; the aqueous phase is decanted and the organic phase is extracted with diethyl ether (2 x 150 cc), dried over anhydrous magnesium sulphate, filtered and concentrated to dryness at 40° C. under reduced pressure (20 mm Hg; 2.7 kPa). The residue obtained is purified by flash-chromatography on a silica column, under a current of argon at medium pressure (0.5-1.5 bar) with a mixture of dichloromethane and methanol (95-5 vol) as eluant. 1-Benzyl-4-hydroxy-4(4-methylphenyl)piperidone (5 g) is obtained in the form of an oil, which is used in the crude state in the subsequent syntheses.

EXAMPLE 47

The experiment is carried out as in Example 1, starting with 2-(3-chloropropyl)naphtho[1,8-cd]isothiazole 1,1-dioxide (6.3 g), 4(3-indolyl)piperidine (4.5 g) and sodium bicarbonate (1.9 g) in a mixture of dimethylformamide (100 cc) and tetrahydrofuran (100 cc). The mixture is heated for 5 hours at boiling point, then cooled to a temperature of about 20° C. Stirring is maintained for 15 hours at this temperature. After purification by flash-chromatography on a silica column, under a current of argon at medium pressure (0.5 - 1.5 bar) with ethyl acetate as eluant, and recrystallization from boiling methyl ethyl ketone (60 cc), 2-{3-[4-(3-indolyl)-piperidino]propyl}naphtho[1,8-cd]isothiazole 1,1-dioxide (2 g) is obtained, m.p. 162° C.

4-(3-Indolyl)piperidine may be prepared according to the method described by J. BERGMAN et al., J. Het. Chem., 1071 (1970).

EXAMPLE 48

The experiment is carried out as in Example 1, starting with 2-(2-chloroethyl)naphtho[1,8-cd]isothiazole 1,1-dioxide (1.2 g), 4-(4-hydroxyphenyl)piperazine dihydrobromide (3.4 g) and sodium bicarbonate (1.3 g) in dimethylformamide (30 cc). The mixture is heated for 4 hours at boiling point, then cooled to a temperature of about 20° C. After purification by flash-chromatography on a silica column, under a current of argon at medium pressure (0.5 - 1.5 bar) with ethyl acetate as eluant, and recrystallization from boiling acetonitrile (90 cc), 2-(2-[4-(4-hydroxyphenyl)-1-piperazin-Yl]ethyl}naphtho[1-,8-cd]isothiazole 1,1-dioxide (1.6 g) is obtained, m.p. 235° C.

EXAMPLE 49

The experiment is carried out as in Example 1, starting with 2-(4-chlorobutyl)na-phtho[1,8-c-]isod-thiazole 1,1-dioxide (3 g), 4-(4-hydroxyphenyl)piperazine dihydrobromide (3.8 g) and sodium bicarbonate (2.8 g) in a mixture of dimethylformamide (30 cc) and tetrahydrofuran (20 cc). The mixture is heated for 5 hours at boiling point, then cooled to a temperature of about 20° C. After purification by recrystallization from boiling acetone 215cc),2-{4-[4-(4-hydroxyphenyl)-1-piperazinyl]-butyl}naphtho[1,8-cd]isothiazole 1,1-dioxide (3.1 g) is obtained, m.p. 195° C.

EXAMPLE 50

The experiment is carried out as in Example 1, starting with 2-(3-chloropropyl)naphtho[1,8-cd]isothiazol 1,1-dioxide (2.1 g), sodium bicarbonate (0.6 g) and 4-(5-fluoro-3-indolyl)-1,2,3,6-tetrahydropyridine(1.6g) in dimethylformamide (15 cc) and tetrahydrofuran (15 cc). The mixture is heated for 5 hours at boiling point, then cooled to a temperature of about 20° C. Stirring is maintained for 7 hours at this temperature. After purification by crystallization from water (50 cc), then recrystallization from a boiling acetone-ethanol mixture (50-50 vol) (50 cc), 2-(3-[4-(5-fluoro-3-indolyl)1,2,3,6-tetrahydro-1-pyridyl]propyl}naphtho[1,8-cd]isothrazole 1,1-dioxide (1.8 g) is obtained, m.p. 224° C.

4-(5-Fluoro-3-indolyl)-1,2,3,6-tetrahydropyridine may be prepared according to the method described by L. NEDELEC et al., Eur. J. Med. Chem., 22, 33 (1987). It has m.p. 175° C.

EXAMPLE 51

The experiment is carried out as in Example 1, starting with 2-(3-chloropropyl)naphtho[1,8-cd]isothiazole 1,1-dioxide (2.4 g), sodium bicarbonate (0.7 g) and 4-(5-chloro-3-indolyl)-1,2,3,6-tetrahydropyridine (2 g) in dimethylformamide (15 cc) and tetrahydrofuran (15 cc). The mixture is heated for 5 hours at boiling point, then cooled to a temperature of about 20° C. Stirring is maintained for 7 hours at this temperature. After purification by crystallization from water (50 cc), then recrystallization from boiling acetonitrile (50 cc), 2-{3-[4(5-chloro-3-indolyl)-1,2,3,6-tetrahydro-1-pyridyl]propyl}naphtho[1,8-cd]isothiazole 1,1-dioxide (2.1 g) is obtained, m.p. 189° C.

4-(5-Chloro-3-indolyl)-1,2,3,6-tetrahydropyridine may be prepared according to the method described by L. NEDELEC et al., Eur. J. Med. Chem., 22, 33 (1987). It has m.p. 220° C.

EXAMPLE 52

The experiment is carried out as in Example 1, starting with 2-(3-chloropropyl)naphtho[1,8-cd]isothiazole 1,1-dioxide (7 g), sodium bicarbonate (4.2 g) and 4-(5-hydroxy-3-indolyl)-1,2,3,6-tetrahydropyridine (5.3 g) in dimethylformamide (50 cc) and tetrahydrofuran (50 cc). The mixture is heated for 5 hours at boiling point, then cooled to a temperature of about 20° C. Stirring is maintained for 7 hours at this temperature. After purification by crystallization from water (100 cc), then recrystallization from a boiling acetoneethanol mixture (50-50 vol) (80 cc), 2-(3-[4-(5-hydroxy 3-indolyl)-1,2,3,6-tetrahydro-1-pyridyl]propyl)naphtho[1,8-cd]isothiazole 1,1-dioxide (5.1 ) is obtained, m.p. 214° C.

4-(5-Hydroxy-3-indolyl)-1,2,.3,6-tetrahydropyridine may be prepared according to the method described by L. NEDELIC et. al., Eur. J. Med. Chem., 22, 23 (1987). It has m.p. 185° C.

EXAMPLE 53

The experiment is carried out as in Example 44, starting with 2-(3-[4-(2-oxo-1-benzimidazolinyl)piperidino]propyl)naphtho[1,8-cd]isothiazole 1,1-dioxide (4.6 g) in dimethylformamide (20 cc) and benzoyl chloride (1.4 g) in tetrahydrofuran (20 cc) and sodium hydride (0.48 g) as a 50% dispersion in vaseline oil. The mixture is stirred for 15 hours at a temperature of about 20° C. After purification by flash-chromatography on a silica column, under a current of argon at medium pressure (0.5-1.5 bar) with a dichloromethane-methanol (90-10 vol) mixture as eluant, and then recrystallization from a boiling acetone/ethanol (90-10 vol) mixture (60 cc), 2-{3-[4-(3-benzoyl-2-oxo-1-benimidazolinyl)-piperidono]propyl}naphtho [1,8]isothiazole 1,1-dioxide (2.9 g) is obtained, m.p. 133° C.

EXAMPLE 54

The experiment is carried out as in Exampe 1, starting with 2-(3-chloropropyl)naphtho[1,8-cd]isothiazole 1,1-dioxide (2.8 g), 4-hydroxy-4-(4-bromophenyl)piperidine (2.4 g) and sodium bicarbonate (0.94 g) in a mixture of dimethylformamide (80 cc) and tetrahydrofuran (50 cc). The mixture is heated for 5 hours to a temperature of about 100° C. then cooled to a temperature of about 20° C. Stirring is maintained for 15 hours at this temperature. After purification by flash-chromatography on a silica column, under a current of argon (0.5-1.5 bar) with a mixture of dichloromethane and methanol (95-5 vol) as eluant, and recrystallization from boiling ethyl acetate (50 cc), 2-(3-[4-(4-bromophenyl)-4-hydroxypiperidino]propylnaphtho[1,8-cd]isothiazole 1,1-dioxide (1.5 g) is obtained in the form of hydrochloride, of m.p. 110 C.

4-Hydroxy-4-(4-bromophenyl)piperidine may be prepared according to the method described in U.S. Pat. No. 3,575,990.

EXAMPLE 55

A mixture of 2-{3-[4-(4-bromophenyl)-4-hydroxypiperidino]propyl}naphtho[1,8-cd]isothiazole 1,1-dioxide (3.7 g), 12 N hydrochloric acid (25 cc) and acetic acid (50 cc) is refluxed under stirring for 16 hours. The solution is then concentrated to dryness at 60° C. under reduced pressure (0.5 mm Hg; 0.07 kPa). The crude reaction product is redissolved in water (25 cc) and neutralized with sodium bicarbonate to pH 7. Extraction of this aqueous phase with dichloromethane (3×50 cc) then drying with magnesium sulphate leads to a brown oil which is purified by flash-chromatography on a silica column, under a current of argon (0.5-1.5 bar) with a mixture of dichloromethane and methanol (98-2 vol) as eluant. After recrystallization from boiling ethanol (30 cc) 2-(3-[4(4-bromophenyl)-1,2,3,6-tetrahydro-1-pyridyl]propyl}naphtho[1,8-cd]isothiazole 1,1-dioxide (1.5 g) is obtained, m.p. 105° C.

EXAMPLE 56

2-(3-Bromo-2-hydroxypropyl)naphtho[1,8-cd]isothiazole 1,1-dioxide (26.8 g), triethylamine (11 cc) and 4(4-fluorophenyl)piperazine (14.1 g) in toluene (280 cc) are heated at boiling point for 8 hours. The mixture is then cooled to a temperature of about 20° C. and stirring is maintained for 15 hours at this temperature. The precipitate formed is separated by filtration and washed with toluene (2 x 50 cc). The filtrate is evaporated to dryness at 40° C. under reduced pressure (20 mm Hg; 2.7 kPa). The residue obtained is purified by chromatography on a silica column, with ethyl acetate as eluant, and recrystallized from boiling acetonitrile (120 cc). 2-(3[4-(4-Fluorophenyl)-1-piperaz-invl]-2-hydroxypropyl}naphtho[1,8-cd]isothiazole 1,1-dioxide (16.2 g) is obtained, m.p. 130° C.

2-(3-Bromo-2-hydroxypropylnaphtho[1,8-cd]isothiazole 1,1-dioxide may be prepared in the following manner: a solution of naphtho[18-cd]isothiazole 1,1-dioxide (41 g) in dimethylformamde (1000 cc) is added over 2 hours under a current of argon to a suspension of sodium hydride (9.6 g) in a 50% dispersion in vaseline oil in dimethylformamide (100 cc), maintaining the temperature between 20 and 35° C. The reaction medium is stirred for 30 minutes at a temperature of about 20° C., then 1,3-dibromo-2-hydroxypropane (20.5 cc) in dimethylformamide (500 cc) is added over 10 minutes. Stirring is maintained for 15 hours at a temperature of about 20° C. The reaction mixture is concentrated to dryness at 70° C under reduced pressure (0.5 mm Hg; 0.07 kPa). The residue is purified by chromatography on a silica column, under a current of argon with a mixture of dichloromethane and methanol (95-5 vol) as eluant. 2-(3-Bromo-2-hydroxypropyl)naphtho[1,8-cd]isothiazole 1, -dioxide (62.1 g) is obtained, in the form of a green oil which is used in the crude state in the subsequent synthesis.

EXAMPLE 57

A solution of 2-(3-[4-(4-fluorophenyl)-1-piperazinyl]-2-hydroxypropyl}naphtho[1,8-cd]isothiazole 1,1-dioxide (4.41 g) in dimethylformamide (50 cc) is poured over 30 minutes into a mixture of sodium hydride (0.53 g) in a 50% dispersion in vaseline oil, and dimethylformamide (10 cc), under a current of argon, maintaining the temperature between 20 and 30° C. The reaction medium is stirred for 1 hour at a temperature of about 20° C. and then methyl iodide (0.7 cc) is added over 10 minutes. Stirring is maintained for 15 hours at a temperature of about 20° C. The mixture is redissolved in distilled water (200 cc) and the organic phase is extracted with dichloromethane (4×100 cc), dried over anhydrous magnesium sulphate, filtered and concentrated to dryness at 40° C. under reduced pressure (20 mm Hg; 2.7 kPa). The residue is purified by flash-chromatography on a silica column, under a current of argon at medium pressure (0.5-1.5 bar) with ethyl acetate as eluant, and recrystallized from boiling acetonitrile (10 cc). 2-(3-[4-(4-Fluoro phenyl)-1-p-iperazinyl]-2-methoxypropyl}naphtho[1,8cd]isothiazole 1,1-dioxide (2.1 g) is obtained, m.p. 128° C.

EXAMPLE 58

2-(2-Bromo-3-[4-(4-fluorophenyl)-1-piperazinyl]propyl)naphtho[1,8-cd]isothiazole 1,1-dioxide (4.2 g), triethylamine (1.1 cc) and dimethylamine (0.5 cc) in toluene (50 cc) are introduced into a 250 cc bomb ap paratus cooled to a temperature of about 0° C. The mixture is stirred and heated for 8 hours to a temperature close to 120° C., then cooled to a temperature of about 20° C. Stirring is continued for 15 hours at this temperature, then the reaction mixture is concentrated to dryness at 40° C. under reduced pressure (20 mm Hg; 2.7 kPa). The residual oil is purified by flash-chromatography on a silica column, under a current of argon at medium pressure (0.5-1.5 bar) with ethyl acetate as eluant. After recrystallization from boiling acetonitrile (15 cc), 2(2-dimethylamino-3-[4-(4-fluorophenyl)-1-piperazinyl]propyl}naphtho[1,8-cd]isothiazole 1,1-dioxide (1.9 g) is obtained, m.p. 118° C.
2-(2-Bromo-3-[4-(4-fluorophenyl)-1-piperazinyl]-propyl}naphtho[1,8-cd]isothiazole 1,1-dioxide may be prepared in the following manner: phosphorus tribromide (1 cc) is poured into 2-{3-[4-(4-fluorophenyl)-1-piperazinyl]-2-hydroxypropyl}naphtho[1,8-cd]isothiazole 1,1dioxide (11.5 g) in toluene (150 cc). The mixture is heated at boiling point for 4 hours, then is cooled to a temperature of about 20° C. The reaction mixture is redissolved in distilled water (300 cc) and alkalinized to pH 11 with N caustic soda (20 cc). The organic phase is extracted with dichloromethane (4×300 cc), dried centrated to dryness at 40° C. under reduced pressure (20 mm Hg; 2.7 kPa). The residual oil is purified by flash-chromatogra-phy on a silica column, under a current of argon at medium pressure (0.5-1.5 bar) with ethyl acetate as diluent. 2-(2-Bromo-3-[4-(4-fluorophenyl)-1-piperazinyl]pripyl}naptho[1,8j-cd]isothiazole 1,1-dioxide (5.7 g) is obtained, m.p. 102° C, which is used in the crude state in the subsequent syntheses.

EXAMPLE 59

The experiment is carried out as in Example 56, starting with 2-(3-chloro-2-methylpropyl)naphtho[1,8-cd]isothiazole 1,1-dioxide (10.4 g), triethylamine (5.1 cc), sodium iodide (5.4 g) and 4-(4-fluorophenyl)piperazine (6.5 g) in toluene (130 cc). The mixture is heated at boiling point for 16 hours, then cooled to a temperature of about 20° C. After purification by flash chromatography on a silica column, under a current of argon at medium pressure (0.5-1.5 bar) with dichloromethane and then ethyl acetate as eluants, and recrystallization from boiling acetonitrile (20 cc), 2-(3-[4-(4-fluorophenyl)-1-piperazinyl]-2-methylpropylnaptho[1,8-cd]isothiazole dioxide (3.1 g) is obtained, m.p. 133° C.
2-(3-Chloro2-methylpropyl)naphtho[1,8-cd]isothiazole 1,1-dioxide may be prepared in the following manner: the experiment is carried out as in Example 56 for the preparation of 2-(3-bromo-2-h ydroxypropyl)-naphtho[1,8-cd]isothiazole 1,1-dioxide, starting with naphtho[1,8-cd]isothiazole 1,1-dioxide (10.3 g) in dimethylformamide (125 cc), sodium hydride (2.4 g) in a 50% dispersion in vaseline oil, and 1-bromo-3-chloro-2methylpropane (5.9 cc). After purification by flash-chromatography on a silica column, under a current of argon at medium pressure (0.5-1.5 bar) with a mixture of dichloromethane and cyclohexane (80-20 vol) as eluant, 2-(3-chloro-2-methylpropyl)naphtho[1,8-cd]isothiazole 1,1-dioxide (10.4 g) is obtained, in the form of a green oil, which is used in the crude state in the subsequent syntheses.

EXAMPLE 60

A solution of naphtho[1,8-cd]isothiazole 1,1-dioxide (3.25 g) in dimethylformamide (50 cc) is poured over 30 minutes into a mixture of sodium hydride (0.76 g) in a 50% dispersion in vaseline oil and dimethylformamide (10 cc), under a current of argon. The reaction medium is stirred for 2 hours at a temperature of about 20° C., then 1-(4-bromo-2-butyl)-4-(4-fluorophenyl)piperazine (5 g) in dimethylformamide (100 cc) is added over 10 minutes., The reaction mixture is stirred for 15 hours at a temperature close to 20° C, then concentrated to dryness at 40° C under reduced pressure (20 mm Hg; 2.7 kPa). The residual oil is purified by flash-chromatography on a silica column, current of argon at medium pressure (0.5-1.5 bar) under a with a mixture of dichloromethane and ethyl acetate (8020 vol) as eluant. After recrystallization.from boiling acetonitrile (13 cc), 2-(3-[4-(4-fluorophenyl)-1-piperazinyl]butyl-}naphtho[1,8-cd]isothiazole 1,1-dioxide 1.g) is obtained, m.p. 122° C.
I -(4-Bromo-2-butyl)-4-(4fluorophenyl)piperazine may be prepared in the following manner: phosphorus tribromide (1.6 cc) is poured into a solution of 1-(4- ) hydroxy-2-butyl)-4-(4-fluorophenyl)piperazine (12.7 g) in toluene (200 cc)..The mixture is heated for 1 hour at a temperature of about 60.C, then is cooled to a temperature close to 20° C. The reaction mixture is redissolved in distilled water (200 cc) and alkalinized to pH 11 with N caustic soda (30 cc). The organic phase is extracted with dichloromethane (2 x 100 cc), dried over anhydrous magnesium sulphate, filtered and concentrated to dryness at 40° C. under reduced pressure (20 mm Hg; 2.7 kPa). The residual oil is purified by flash-chromatography on a silica column, under a current of argon at medium pressure (0.5-1.5 bar) with a mixture of ethyl acetate and methanol (50-50 vol) as eluant 1-(4-Bromo2-b.tuyl)-4-(4fluorophenyl)piperazine (5 g) is obtained, in the form of a pale yellow oil, which is used in the crude state in the subsequent syntheses.
1-(4-Hydroxy-2-butyl)-4-(4-fluorophenyl)piperazine may be prepared in the following manner: 3-bromobutanol (29 g), triethylamine (26.6 cc) and 4-(4-fluorophenyl)piperazine (34 g) in toluene (800 cc) are heated at boiling point for 8 hours. The mixture is then cooled
° C and stirring is maintained for 15 hours at this temperature. The precipitate formed is separated by filtration and washed with toluene (2×50 cc). The filtrate is redissolved in distilled water (400 cc), the organic phase is decanted, dried over anhydrous magnesium sulphate and concentrated to dryness at 40° C under reduced pressure (20 mm Hg; 2.7 kPa). The residual oil is purified by flash-chromatography on a silica column, under a current of argon at medium pressure (0.5-1.5 bar) with ethyl acetate and then a mixture of ethyl acetate and methanol (95-5 vol) as eluant. 1-(4-Hydroxy-2-butyl)-4-(4-fluorophenyl) piperazine (12.7 g) is obtained, in the form of a yellow oil, which is used in the crude state in the subsequent syntheses.
3-Bromobutanol. may be prepared according to the method described by D.A. PALAVANDISHVILI et al., Chem. abstr., 70, 106089.

EXAMPLE 61

The experiment is carried out as in Example 56, starting with 2-(4-bromo-2-butyl)naphtho[1,8-cd]isothiazole 1,1-dioxide (5.2 g), triethylamine (2.1 cc) and 4-(4-fluorophenyl)piperazine (2.8 g) in toluene (200 cc). The mixture is heated at boiling point for 8 hours and then cooled to a temperature of about 20° C. After purification by flash-chromatography on a silica column, under a current of argon at medium pressure (0.5-1.5 bar) with a mixture of dichloromethane and ethyl acetate (90-10 as eluant, crystallization from isopropyl oxide (30 cc) and recrystallization from boiling acetonitrile (10 cc), 2-{4-[4-(4-fluorophenyl)-1-piperazinyl]-2butyl)naphtho[1,8-cd]isothiazole 1,1-dioxide (1.2 g) is obtained, m.p. 116° C.
2-(4-Bromo-2-butyl)naphtho[1,8-cd]isothiazole 1,1-dioxide may be prepared in the following manner: phosphorus tribromide (1.8 cc) is poured into a solution of 2-(4-hydroxy-2-butyl)naphtho[1,8-cd]isothiazole 1,1-dioxide (16.1 g) in toluene (250 cc). The mixture is heated for 2 hours at a temperature of about 60° C. then cooled to a temperature close to 20° C. The reaction mixture is redissolved in distilled water (200 cc), the organic phase is extracted with toluene (3×50 cc), dried over anhydrous magnesium sulphate, filtered and concentrated to dryness at 40° C. under reduced pressure (20 mm Hg; 2.7 kPa). 2-(4-Bromo-2-butyl)naphtho[1,8-cd]isothiazole 1,1-dioxide (5.2 g) is obtained, in the form of a brown oil, which is used in the crude state in the subsequent syntheses.

2-(4-Hydroxy-2-butyl)naphtho[1,8-cd]isothiazole 1,1-dioxide may be prepared in the following manner: the experiment is carried out as in Example 56 for the preparation of 2-(3-bromo-2-hydroxy-1-propyl)naphtho[1,8cd]isothiazole 1,1-dioxide, starting with naphtho[1,8cd]isothiazole 1,1-dioxide (49.6 g) in dimethylformamide (350 cc), sodium hydride (11.6 g) in a 50% dispersion in vaseline oil, and 2-bromobutanol (37.1 g). After purification by flash-chromatography on a silica column, under a current of argon at medium pressure (0.5–1.5 bar) with a mixture of dichloromethane and ethyl acetate (50–50 vol) as eluant, 2-(4-hydroxy-2-butyl)naphtho[1,8-cd]isothiazole 1,1-dioxide (16.g) is obtained, in the form of a brown oil, which is used in the crude state in the subsequent syntheses.

The pharmaceutical compositions of the invention are constituted by a compound of formula (I) in the free form or I0 in the form of an addition salt with a pharmaceutically acceptable acid, in the pure state or in the form of a composition in which it is associated with any other pharmaceutically compatible product, which may be inert, eg. a carrier or coating, or physiologically active. The medicaments according to the invention may be used orally, parenterally, rectally or topically.

Tablets, pills, powders (gelatine capsules, sachets) or granules may be used as solid compositions for oral administration. In these compositions, the active principle according to the invention is mixed with one or more inert diluents, such as starch, cellulose, sucrose, lactose or silica, under a current of argon. These compositions may also contain substances other than diluents, for example one or more lubricants such as magnesium stearate or talc, a colorant, a coating (sugar-coated pills) or a varnish.

Pharmaceutically acceptable solutions, suspensions, emulsions, syrups and elixirs containing inert diluents such as water, ethanol, glycerol, vegetable oils or paraffin oil may be used as liquid compositions for oral administration. These compositions may contain substances other than diluents, for example wetting, sweetening, thickening, flavoring or stabilizing products.

Sterile compositions for parenteral administration may preferably be aqueous or nonaqueous solutions, suspensions or emulsions. Water, propylene glycol, polyethylene glycol, vegetable oils, in particular olive oil, injectable organic esters, for example ethyl oleate, or other suitable organic solvents may be used as solvent or vehicle. These compositions may also contain adjuvants, in particular wetting, isotonifying, emulsifying, dispersing and stabilizing agents. Sterilization may carried out in several ways, for example by aseptic filtration, by incorporating sterilizing agents into the composition, by irradiation or by heating. The sterile compositions may also be prepared in the form of sterile solid compositions which can be dissolved at the moment of use in sterile water or any other sterile injectable medium.

The compositions for rectal administration are suppositories or rectal capsules which contain, in addition to the active product, excipients such as cocoa butter, semi-synthetic glycerides or polyethylene glycols.

The compositions for topical administration may be for example creams, ointments, lotions, collyria, collutories, nasal drops or aerosols.

In human therapeutics, the compounds according to the invention are particularly useful for the treatment of ailments in which serotonin is involved, and in particular ailments of the central nervous system, the cardiovascular system and intestinal disorders. They are particularly useful for the treatment of anxiety, sleeping disorders, depression, psychoses and in particular schizophrenia, migraine, asthma, hypertension and urticaria, as analgesics and as inhibitors of platelet aggregation.

Doses depend on the required effect, on the length of treatment and on the administration route used; they are generally between 10 and 300 mg per day by the oral route for an adult, with single doses ranging from 2 to 100 mg of active substance.

The doctor will generally determine the appropriate posology as a function of the age, the weight and all other factors of the subject to be treated.

The following examples illustrate some compositions according to the invention:

EXAMPLE A

Soft capsules containing 50 mg of active product are prepared, according to the normal technique, with the following composition:

| | |
|---|---|
| 2-{3-[4-(4-fluorophenyl)-1-piperazinyl]-2-hydroxypropyl}naphtho[1,8-cd]isothiazole 1,1-dioxide | 50 mg |
| cellulose | 18 mg |
| lactose | 55 mg |
| colloidal silica, under a current of argon | 1 mg |
| sodium carboxymethylstarch | 10 mg |
| talc | 10 mg |
| magnesium stearate | 1 mg |

EXAMPLE B

Tablets containing 50 mg of active product are prepared, according to the normal technique, with the following composition:

| | |
|---|---|
| 2-{3-[4-(4-fluorophenyl)-1-piperazinyl]-2-methoxypropyl}naphtho[1,8-cd]isothiazole 1,1-dioxide | 50 mg |
| lactose | 104 mg |
| cellulose | 40 mg |
| polyvidone | 10 mg |
| sodium carboxymethylstarch | 22 mg |
| talc | 10 mg |
| magnesium stearate | 2 mg |
| colloidal silica, under a current of argon | 2 mg |
| mixture of hydroxymethylcellulose, glycerine and titanium oxide (72-3.5-24.5) | quantity sufficient for 1 tablet coated to finish at 245 mg |

EXAMPLE C

An injectable solution containing 10 mg of active product is prepared with the following composition:

| | |
|---|---|
| 2-{2-dimethylamino-3-[4-(4-fluorophenyl)-1-piperazinyl]propyl}naphtho[1,8-cd]isothiazole 1,1-dioxide | 10 mg |
| benzoic acid | 80 mg |
| benzyl alcohol | 0.06 cc |
| sodium benzoate | 80 mg |
| 95% ethanol | 0.4 cc |
| sodium hydroxide | 24 mg |
| propylene glycol | 1.6 cc |
| water | quantity sufficient to produce 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula

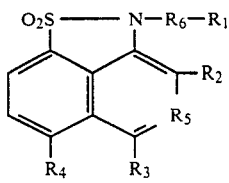

in which $R_1$ represents a 1,2,3,6-tetrahydro-1-pyridyl radical substituted in the 4-position by (a) a phenyl radical, (b) a phenyl radical substituted by a halogen atom or an alkyl, hydroxy or alkoxy radical, (c) a 3-indolyl radical, (d) a 3-indolyl radical substituted on the nitrogen atom by an alkyl or alkylcarbonyl radical and/or in the 5-position by a chlorine or fluorine atom or (e) a 3-(5-hydroxyindolyl) radical.

a 1-piperazinyl radical substituted in the 4-position by (a) a phenyl radical, (b) a phenyl radical substituted by an alkoxy, alkyl, hydroxy, nitro or amino radical or a halogen atom, (c) a 1,2-benzisothiazol-3-yl radical, (d) a 1,2benzisoxazol-3-yl radical or (e) a 2-pyridyl radical, a piperidino radical substituted in the 4-position by (a) a phenyl radical, (b) a phenyl radical substituted by a halogen atom or a hydroxy, alkyl or alkoxy radical, (c) two phenyl radicals, (d) a bis(4-fluorophenyl)methylene radical, (e) a 4-fluorobenzoyl radical, (f) a 2-oxo-1-benzolinyl radical, (g) a 2-oxo-1-benzimidazolinyl radical substitutes in the 3-position by an alkylcarbonyl or benzoyl radical, (h) a hydroxy radical and a phenyl radical optionally substituted by an alkyl, alkoxy or hydroxy radical or a halogen atom, (i) a 3-indolyl radical, (j) a 3-indolyl radical substituted on the nitrogen atom by an alkyl or alkylcarbonyl radical and/or in the 5-position by a chlorine or fluorine atom or (k) a 3-(5-hydroxyindolyl) radical.

either:

$R_2$ and $R_3$, which are identical, represent a hydrogen or halogen atom and $R_4$ represents a hydrogen atom or $R_2$ and $R_4$ represent a hydrogen atom and $R_3$ represents a halogen atom or an acetylamino radical or $R_2$ and $R_3$ represent a hydrogen atom and $R_4$ represents a halogen atom and $R_5$ represents a —CH= group, $R_6$ represents an alkylene chain containing 2 to 4 carbon atoms or a propylene chain substituted in the 1- or 3-position by an alkyl radical or in the 2-position by an alkyl, alkoxy, hydroxy, dialkylamino, piperidono, morpholino or thiomorpholino radical, with the reservation that when $R_6$ represents a propylene radical substituted in the 2-position by a dialkylamino, piperidino, morpholino or thiomorpholino radical, $R_1$ cannot be a radical containing a hydroxy radical and it being understood that the alkyl and alkoxy radicals and the alkyl and alkoxy portions contain 1 to 4 carbon atoms in a straight or branched chain, or its salt with inorganic and organic acid.

2. A compound according to claim 1 in which the halogen atoms are chlorine or bromine atoms.

3. A compound according to claim 1 in which $R_1$ represents a 1,2,3,6-tetrahydro-1-pyridyl radical substituted in the 4-position by a halophenyl radical, a phenyl radical or a 3-indolyl radical substituted on the nitrogen atom by alkyl or alkylcarbonyl radical, a 1-piperazinyl radical substituted in the 4-position by a 2-pyridyl radical, 1,2-benzisothiazol-3-yl radical or phenyl radical substituted by a halogen atom or a hydroxy, amino or alkyl radical or a piperidino radical substituted in the 4-position by a phenyl or N-alkyl-3-indolyl radical.

4. A pharmaceutical composition useful for the treatment of ailments in which serotonin is implicated comprising an effective amount of at least one compound according to claim 1 in the free form or in the form of an addition salt with a compatible, pharmaceutically acceptable carrier or coating.

5. A method for the treatment of ailments in which serotonin is implicated which comprises administering to a subject in need of such treatment, an effective amount of a compound according to claim 1 in the free form or in the form of an addition salt with pharmaceutically acceptable salt.

6. 2-{3-[4-(4-fluorophenyl)-1-piperazinyl]propyl} naphtho [1,8-cd]isothiazole-1,1-dioxide.

* * * * *